(12) United States Patent
Brown et al.

(10) Patent No.: US 8,920,493 B2
(45) Date of Patent: Dec. 30, 2014

(54) SYSTEMS AND METHODS FOR HOLDING ANNULOPLASTY RINGS

(75) Inventors: Laura-Lee Brown, Maplewood, MN (US); Rebecca Volovsek, Hudson, WI (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 244 days.

(21) Appl. No.: 13/234,860

(22) Filed: Sep. 16, 2011

(65) Prior Publication Data
US 2013/0073031 A1 Mar. 21, 2013

(51) Int. Cl.
*A61F 2/24* (2006.01)

(52) U.S. Cl.
CPC ....... *A61F 2/2466* (2013.01); *A61F 2250/0019* (2013.01); *A61F 2/2448* (2013.01)
USPC .......................................... 623/2.11; 623/2.36

(58) Field of Classification Search
USPC ..................... 623/2.11, 2.36–2.42
See application file for complete search history.

(56) References Cited

U.S. PATENT DOCUMENTS

| | | | |
|---|---|---|---|
| 3,656,185 A | 4/1972 | Carpentier | |
| 4,042,979 A | 8/1977 | Angell | |
| 4,055,861 A | 11/1977 | Carpentier et al. | |
| 4,703,676 A | 11/1987 | Mayer | |
| 4,743,253 A | 5/1988 | Magladry | |
| 4,865,600 A * | 9/1989 | Carpentier et al. | 623/2.11 |
| 4,932,965 A | 6/1990 | Phillips | |
| 5,011,481 A | 4/1991 | Myers et al. | |
| 5,061,277 A | 10/1991 | Carpentier et al. | |
| 5,089,015 A | 2/1992 | Ross | |
| 5,104,407 A | 4/1992 | Lam et al. | |
| 5,290,243 A | 3/1994 | Chodorow et al. | |
| 5,306,296 A | 4/1994 | Wright et al. | |

(Continued)

FOREIGN PATENT DOCUMENTS

| | | |
|---|---|---|
| EP | 0338994 A1 | 10/1989 |
| EP | 0495417 A1 | 7/1992 |

(Continued)

OTHER PUBLICATIONS

Vongpatanasin, W., et al., "Prosthetic Heart Valves", The New England Journal of Medicine, vol. 335, No. 6, pp. 407-416 (1996).

(Continued)

*Primary Examiner* — David Isabella
*Assistant Examiner* — Suba Ganesan
(74) *Attorney, Agent, or Firm* — Lerner, David, Littenberg, Krumholz & Mentlik, LLP

(57) ABSTRACT

Holders for releasably holding annuloplasty rings prior to and during the implantation of the rings employ any of a variety of features relating to such things as holder shape, handle attachment structures, securement of a ring to the holder, and release of the ring from the holder. In one aspect, the holder includes a flexible bracket and a more rigid connector. In another aspect, the holder includes a flexible bracket and cutting blocks, wherein the interior surface of the cutting block is made of a higher durometer material than the bracket. The interior surface of the cutting block can be coated with a higher durometer material than the material of the bracket. In another aspect, the holder includes a flexible bracket and cutting blocks made of a higher durometer material than the flexible bracket.

18 Claims, 23 Drawing Sheets

(56) References Cited

U.S. PATENT DOCUMENTS

| | | |
|---|---|---|
| 5,350,420 A | 9/1994 | Cosgrove et al. |
| 5,403,305 A | 4/1995 | Sauter et al. |
| 5,415,667 A | 5/1995 | Frater |
| 5,509,918 A | 4/1996 | Romano |
| 5,522,884 A | 6/1996 | Wright |
| 5,607,471 A | 3/1997 | Seguin et al. |
| 5,653,716 A | 8/1997 | Malo et al. |
| 5,669,919 A | 9/1997 | Sanders et al. |
| 5,800,531 A | 9/1998 | Cosgrove et al. |
| 5,814,097 A | 9/1998 | Sterman et al. |
| 5,814,101 A | 9/1998 | Wallner et al. |
| 5,824,066 A | 10/1998 | Gross |
| 5,843,177 A | 12/1998 | Vanney et al. |
| 5,888,240 A | 3/1999 | Carpentier et al. |
| 5,919,191 A | 7/1999 | Lennox et al. |
| 5,972,030 A | 10/1999 | Garrison et al. |
| 6,001,127 A | 12/1999 | Schoon et al. |
| 6,019,739 A | 2/2000 | Rhee et al. |
| 6,143,024 A | 11/2000 | Campbell et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,283,993 B1 | 9/2001 | Cosgrove et al. |
| 6,319,280 B1 | 11/2001 | Schoon |
| 6,368,348 B1 | 4/2002 | Gabbay |
| 6,391,054 B2 | 5/2002 | Carpentier et al. |
| 6,406,492 B1 | 6/2002 | Lytle |
| 6,409,758 B2 | 6/2002 | Stobie et al. |
| 6,451,054 B1 | 9/2002 | Stevens |
| 6,564,805 B2 | 5/2003 | Garrison et al. |
| 6,602,289 B1 | 8/2003 | Colvin et al. |
| 6,629,534 B1 | 10/2003 | St. Goar et al. |
| 6,689,163 B2 | 2/2004 | Lytle |
| 6,702,852 B2 | 3/2004 | Stobie et al. |
| 6,719,786 B2 | 4/2004 | Ryan et al. |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,761,733 B2 | 7/2004 | Chobotov et al. |
| 6,786,924 B2 | 9/2004 | Ryan et al. |
| 6,893,459 B1 | 5/2005 | Macoviak |
| 6,942,694 B2 | 9/2005 | Liddicoat et al. |
| 8,052,748 B2 | 11/2011 | Schoon et al. |
| 2001/0010018 A1 | 7/2001 | Cosgrove et al. |
| 2002/0129820 A1 | 9/2002 | Ryan et al. |
| 2002/0133180 A1 | 9/2002 | Ryan et al. |
| 2002/0173844 A1 | 11/2002 | Alfieri et al. |
| 2002/0183839 A1 | 12/2002 | Garrison et al. |
| 2003/0045929 A1 | 3/2003 | McCarthy et al. |
| 2003/0050693 A1 | 3/2003 | Quijano et al. |
| 2003/0093148 A1 | 5/2003 | Bolling et al. |
| 2003/0125715 A1 | 7/2003 | Kuehn et al. |
| 2003/0135270 A1* | 7/2003 | Breznock ............... 623/2.42 |
| 2003/0144732 A1 | 7/2003 | Cosgrove et al. |
| 2003/0176916 A1 | 9/2003 | Ryan et al. |
| 2003/0176917 A1 | 9/2003 | Ryan et al. |
| 2003/0199975 A1 | 10/2003 | Gabbay |
| 2004/0006384 A1 | 1/2004 | McCarthy |
| 2004/0013327 A1 | 1/2004 | Mukai et al. |
| 2004/0018656 A1 | 1/2004 | Tsai |
| 2004/0019357 A1 | 1/2004 | Campbell et al. |
| 2004/0034410 A1* | 2/2004 | Holmberg ............... 623/2.11 |
| 2004/0249453 A1 | 12/2004 | Cartledge et al. |
| 2005/0267572 A1* | 12/2005 | Schoon et al. ............... 623/2.11 |
| 2007/0156234 A1 | 7/2007 | Adzich et al. |
| 2008/0188861 A1 | 8/2008 | Ryan et al. |

FOREIGN PATENT DOCUMENTS

| | | |
|---|---|---|
| EP | 2520250 A1 | 11/2012 |
| WO | 9117721 A1 | 11/1991 |
| WO | 0059408 A1 | 10/2000 |
| WO | 02074197 A2 | 9/2002 |
| WO | 03020178 A1 | 3/2003 |
| WO | 03053289 A1 | 7/2003 |
| WO | 2005112832 A1 | 12/2005 |

OTHER PUBLICATIONS

Ahmadi, A, et al., Hemodynamic Changes Following Experimental Production and Correction of Acute Mitral Regurgitation With an Adjustable Ring Prosthesis, The Thoracic and Cardiovascular Surgeon, vol. 36, No. 6, pp. 313-319 (1988).
Alonso-Lej, F The dynamic' mitral ring: A new concept in treating mitral insufficiency Recent Progress in Mitral Valve Disease, pp. 45 and 443-449 (1984).
Belcher, J.R. "The Surgical Treatment of Mitral Regurgitation" British Heart Journal vol. 26, pp. 513-523 (1964).
Bolling, S.F., et al., "Surgery for Acquired Heart Disease", The Journal of Thoracic and Cardiovascular Surgery, vol. 109, No. 4, pp. 676-683 (1995).
Bolling. S.F., Mitral Reconstruction in Cardiomyopathy, The Journal of Heart Valve Disease, vol. 11, Suppl. 1, pp. S26-S31 (2002).
Carpentier, A., et al., "A New Reconstructive Operation for Correction of Mitral and Tricuspid Insufficiency", The Journal of Thoracic and Cardiovascular Surgery, vol. 61, No. 1, pp. 1-13 (1971).
Carpentier, A.,"La Valvuloptastie Technique de Valvuloplastie Mitra Recanstitutive: Une Nouvelle le", Technique Chirugicale, No. 7, pp. 251-255 (1969).
Carpentier, A.F., et al., The Physlo-Ring: An Advanced Concept in Mitral Valve Annuloplasty, Ann. Thorac. Surg. vol. 60, No. 5, pp. 1177-1186 (1995).
Castells, E., et al., tong-Term Results With the Puig Massana-Shiley Annuloplasty Ring, The Journal of Cardiovascular Surgery, Abstracts, vol. 24 No. 4, p. 387 (1983).
Chachques, J.C. et al.' "Absorbable Rings for Pediatric Valvuloplasty: Preliminary Study", Supplement IV to Circulation, vol. 82, No. 5, pp. IV-82-IV-88 (1990).
Cooley, D.A., "Ischemic Mitral Insufficiency", Cardiac Surgery: State of the Art Reviews, vol. 6, No. 2, pp. 237-249 (1992).
Cooley, D.A., et al., "A Cost-Effective Dacron Annuloplasty Ring", The Annals of Tharacic Surgery, vol. 56. pp. 185-186 (1993).
Cooley, D.A., et al., "Mitral Leaflet Prolapse: Surgical Treatment using Posterior Annular Collar Prosthesis", Cardiovascular Diseases Bulletin of the Texas Heart Institute, vol. 3, No. 4, pp. 438-443 (1976).
Cosgrove, D.M. III, et al, "Initial Experience With the Cosgrove-Edwards Annuloplasty System", The Annals of Thoracic Surgery, vol. 60, pp. 499-504 (1995).
CySapuico, et al., "AHHYl1OrlACTNKA TPNKYCHNOArJbHOr'O KrIAI1AHA PEr'YHNPYEMbIM UOrlYKOHbUOM 1100 KOHTPOHEM YPECrINWEBOOHON EXOKAPONOrPA4~NN", KOHIIEKTNB ABTOPOB (1992).
Deloche, A., et al., Valve Repair With Carpentier Techniques, The Journal of Thoracic and Cardiovascular Surgery, vol. 99, No. 6, pp. 990-1002 (1990).
Duran, C.G., Reconstructive procedure of the Mitral Valve Including Ring Annuloplasty, Modern Technics in Surgery, 20 (1979).
Duran, C.G., et al., "Clinical and Hemodynamic Performance of a Totally Flexible Prosthetic Ring for Atrioventricular Valve Reconstruction", The Annals of Thoracic Surgery, vol. 22, No. 5. pp. 458-463 (1976).
Duran, C.G., et al., "Stability of Mitral Reconstructive Surgery at 10-12 Years for Predominantly Rheumatic Valvular Disease", Circulation Supplement I, vol. 78, No. 3, pp. 1-91-1-96 (1988).
Duran, C.M.G., et al., Valve Repair in Rheumatic Mitral Disease~, Supplement to Circulation vol. 84, No. 5, pp. III 125-III 132 (1990).
Durán, C.M.G., et al., A New Absorbable Annuloplasty Ring in the Tricuspid Position: An Experimental Studl, The Thoracic and Cardiovascular Surgeon, vol. 34, No. 6, pp. 377-379 (1986).
Erk, M.K., "Morphological and Functional Reconstruction of the Mitral Valve: A New Annuloplastic Procedure," Texas Heart Institute Journal, vol. 9, pp. 329-334 (1982).
Erk, M.K., et al., "Semi-frame Mitral Annuloplasty", Cardiac Reconstructions pp. 157-163 (1989).

(56) References Cited

OTHER PUBLICATIONS

Fundaro, P., et al., "Polytetrafluoroethylene Posterior Annuloplasty for Mitral Regurgitation", The Annals of Thoracic Surgery, Correspondence, vol. 50, No. 1, pp. 165-166 (1990).

Ghosh, P.K., !IMitral Annuloplasty: A Right-Side View, The Journal of Heart Valve_Disease,_vol.5,_pp._286-293_(1996).

Gorton, M.E. et al "Mitral Valve Repair Using a Flexible and Adjustable Annuloplasty Ring," The Annals of Thoracic Surgery, vol. 55, pp. 860-863 (1993).

Gregori, F., Jr., et al., "Urn Novo Modelo De Mel Protetico Para Pacientes Corn Insuficiencia Valvar Mitral. Relato de Dois Casos", Arguivos Brasileiros de Cardiologia, vol. 50, No. 6, pp. 41 7-420 (1988).

Gregori, F., et al., "Mitral Valvuloplasty With a New Prosthetic Ring". Official Journal of the European Association br Cardia-thoracic surgery, vol. 8, No. 4, pp. 168-172 (1994).

Hendren, W.G., et al., "Mitral Valve Repair for Ischemic Mitral Insufficiency", The Annals of Thoracic Surgery, vol. 52, pp. 1246-1252 (1991).

Henze, A., et al., "The Adjustable Half-Moon: An Alternative Device for Tricuspid Valve Annuloplasty", Scandinavian Journal of Thoracic and Cardiovascular Surgery, vol. 18, pp. 29-32 (1984).

Kasegawa, H., et al ., "Physiologic Remodeling Annutoplasty to Retain the Shape of the Anterior Leaflet: A New Concept in Mitral Valve Repair", The Journal of Heart Valve Disease. vol. 6, pp. 604-607 (1997).

Katz, N.M., "Current Surgical Treatment of Valvular Heart Disease", American Family Physician, vol. 52, No. 2, pp. 559-568 (1995).

Kaye, D.M., et al., "Feasibility and Short-Term Efficacy of Percutaneous Mitral Annular Reduction for the Therapy of Heart Failure—Induced Mitral Regurgitation, Circulation, Brief Rapid Communication", No. 108, pp. 1795-1797 (2003).

Kurosawa, H., et al.,~Mitral Valve Repair by Carpentier-Edwards Physio Annuloplasty Ring, The Japanese Journal of Thoracic and Cardiovascular Surgery, vol. 47, pp. 355-360 (1999).

Lachrnann, J., MD, et al., "Mitral Ring Annuloplasty: An Incomplete Correction of Functional Mitral Regurgitation Associated with Left Ventricular Remodeling", Current Cardiology Reports. vol. 3, pp. 241-246 (2001).

Levine, R.A., et al., "The Relationship of Mitral Annular Shape to the Diagnosis of Mitral Valve Prolapse", Circulation, vol. 75, No. 4, pp. 756-767 (1987).

Martin, S. L., et al., Echocardiographic Evaluation of Anuloplasty Rings: Comparison of Continuity Equation and Pressure Half-Time Methods, Journal of the American Society of Echocardiography, vol. 5, No. 3, p. 322(1992).

Melo, J.Q., et al. Surgery for Acquired Heart Disease: Atrioventricular Valve Repair Using Externally Adjustable Flexible Rings°, The Journal of Thoracic and Cardiovascular Surgery No. 110, pp. 1333-1337 (1995).

Morse, et al., "Cardiac Valve Identification Atlas and Guide", Chapter IOin Guide to Prosthetic Cardiac Valves, edited by Dryden Morse, Robert M. Steiner, and Javier Fernandez, Springer-Verlag New York Inc. (1985).

Murphy, J. P. et al., "The Puig-Massana-Shiley Annuloplasty Ring for Mitral Valve Repair: Experience in 126 Patients," The Annals of Thoracic Surgery, vol. 43, pp. 52-58 (1987).

Ogus, T.N., et al., !!Posterior Mitral Annuloplasty with an Adjustable Homemade Ring, Journal of Cardiac Surgery, vol. 17, No. 3, pp. 226-228 (2002).

Pellegrini, A., et al., "Posterior Annuloplasty in the Surgical Treatment of Mitral Insufficiency", The Journal of Heart Valve Disease, vol. 2, pp. 633-638 (1993).

Reece, et al., "Surgical Treatment of Mitral Systolic Click Syndrome: Results in 37 Patients", The Annals of Thoracic Surgery, vol. 39, No. 2, pp. 155-1 58 (1985).

Rubenstein, F., et al., "Alternatives in Selection of Rings for Mitral Annuloplasty", Current Opinon in Cardiology, vol. 16, No. 2, pp. 136-139 (2001).

Salati, M. et al., "Annular Remodelling With Pericardial Reinforcement: Surgical Technique and Early Results," The Journal of Heart Valve Disease, vol. 2, pp. 639-641 (1993).

Salati, M., et al Posterior Pericardial Annuloplasty: A Physiological Correction?, European Journal of Cardio-Thoracic Surgery, vol. 5, pp. 226-229(1991).

Salvador, L. et al., The Pericardium Reinforced Suture Annuloplasty: Another Tool Available for Mitral Annulus Repair, Journal of Cardiac Surgery, vol. 8, pp. 79-84 (1993).

Shumway, S.J., et al., A 'Designer' Annuloplasty Ring for Patients with Massive Mitral Annular Dilation, The Annals of Thoracic Surgery, vol. 46, No. 6, pp. 695-696 (1988).

Smolens, I., et al., Current Status of Mitral Valve Reconstruction in Patients with Dilated Cardiomyopath~', Ital. Heart J., vol. 1, No. 8, pp. 517-520 (2000).

Victor, S. et al., "Truly Flexible D-Shaped Autogenous Pericardial Ring for Mitral Annuloplasty," The Annals of Thoracic Surgery, vol. 56, pp. 179-180 (1993).

International Search Report for Application No. PCT/US2012/054587 dated Nov. 28, 2012.

* cited by examiner

SYSTEMS AND METHODS FOR HOLDING ANNULOPLASTY RINGS

FIELD OF THE INVENTION

This invention relates generally to holding devices for implantable medical prostheses or devices, and more specifically to flexible holding devices for securing and supporting annuloplasty rings to be implanted adjacent to mitral or tricuspid valves.

BACKGROUND OF THE INVENTION

Annuloplasty rings are useful in a variety of medical procedures, such as strengthening the base annulus of mitral and tricuspid valves in the heart. Heart disease may result in disorders of the cardiac valves characterized by weakening or loosening of the heart muscle tissue forming and surrounding the heart valves. The mitral and tricuspid valves respectively allow blood to flow from the heart's left and right atria into the heart's left and right ventricles. Weakening of heart tissues may cause these valves to function improperly. In particular, these valves may no longer close completely, allowing blood to be regurgitated back through the valve during ventricle contraction. An annuloplasty ring may be used to provide support to the base annulus of a cardiac valve, restoring the ability of the valve to close and seal itself adequately. The ring prevents the base annulus of the valve from deforming, thereby reducing or eliminating regurgitation through the valve.

The implantation of an annuloplasty ring on a cardiac valve may require open-heart or less invasive surgery. During surgery, the implanted ring is mounted on a specially designed holder which is used to secure and maintain the shape of the ring while the ring is placed into the heart and is sutured to the valve annulus. The holder may also be used to secure and support the ring during storing, transportation, and other manipulations surrounding the implantation procedure. The holder is typically detached from the ring during the ring implantation procedure, and is removed from the implantation site.

U.S. Pat. No. 5,041,130, U.S. Pat. No. 5,011,481, and U.S. Pat. No. 6,001,127 show and describe annular and C-shaped annuloplasty ring holders.

SUMMARY OF THE INVENTION

The present invention provides apparatus and methods for securing and supporting annuloplasty rings during implantation of the rings and during related procedures. The apparatus may include a specially designed holder to which the ring can be releasably secured.

The holder may be planar or saddle-shaped, and may be shaped so as to approximate the shape of the implanted ring. The holder may also be flexible, semi-flexible, or rigid. The holder may include holes or be structured so as to increase the visibility of the valve and surrounding area through or around the holder. A connector may be mounted on the holder to allow the holder to be manipulated by the physician. The connector may be placed, shaped, or recessed so as to increase visibility of the operative area, to improve access to the area, or to suit other objectives.

The ring may be secured to the holder using a variety of means and methods. Suture threads may be used to tie the ring to the holder. Threads may be stitched through, or looped or wrapped around either or both of the ring and holder. Suture threads may be released using cutting blocks indicating locations for or guiding the cutting of the threads. In a flexible holder, especially, the cutting blocks may include higher durometer material, as compared to the material of the bracket. Cutting blocks may be located or recessed at various locations on the holder, may be shaped to suit a variety of objectives, and may incorporate knot tying posts where suture thread may be tied. Suture threads may also be released using other methods. The ring may also be secured to the holder using internal tension or clamping means. A variety of holders functioning on these principles are presented.

BRIEF DESCRIPTION OF THE DRAWINGS

Further features of the invention, its nature, and various advantages will be more apparent from the following detailed description and the accompanying drawings, in which.

Figure 1:
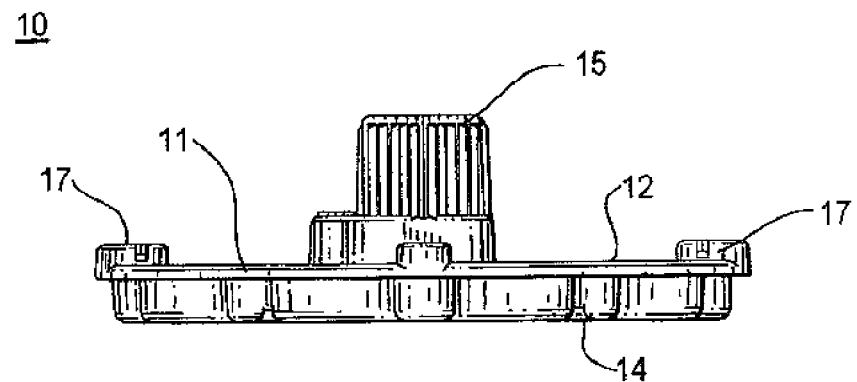
FIG. 1 is a side view of an illustrative planar annuloplasty ring holder in accordance with the invention.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives.

DETAILED DESCRIPTION

This invention describes embodiments of a holder for an annuloplasty ring. An annuloplasty ring may be used by a surgeon to assist in strengthening or reshaping a heart valve. An annuloplasty ring may be sutured to the heart adjacent to, for example, the mitral valve to reshape the valve. This procedure may be used to treat and limit valve regurgitation, or any other valve malfunction. Before and during implantation of the annuloplasty ring into the patient, the ring is mounted on a holder which is used to secure and support the ring as it is placed and sutured into the heart. The holder may be stiff or flexible, and may alternatively be used during open-heart or minimally invasive surgery. A flexible holder may be especially well-suited for minimally invasive surgery, during which the holder and ring may have to be inserted into the patient's heart through a small incision and/or catheter. The holder may also be used to support the ring during storage, manipulation or other procedures surrounding annuloplasty ring implantation and preparation. In a preferred embodiment, the holder is not implanted into the patient. Instead, the holder is detached from the ring during the implantation procedure and is removed from the implant site. The ring holder may be manipulated by the surgeon using a handle or other grasping device that attaches to a connector included on the ring holder.

The following specification describes various novel features that may be incorporated into a ring holder. These features may include, for example, alternate holder structures, connector structures, cutting blocks and suture tying posts, flexible brackets, suture and non-suture methods of attaching the ring to the holder, as well as pre-stitched sutures. Such features are described in the associated titled sections of the following description.

Those skilled in the art will appreciate that while the invention is described with regard to holders specifically designed for annuloplasty rings, the invention may be used in the more general context of designing mounting brackets for a variety of medical and other applications.

A. Holder Structure

Figure 2:
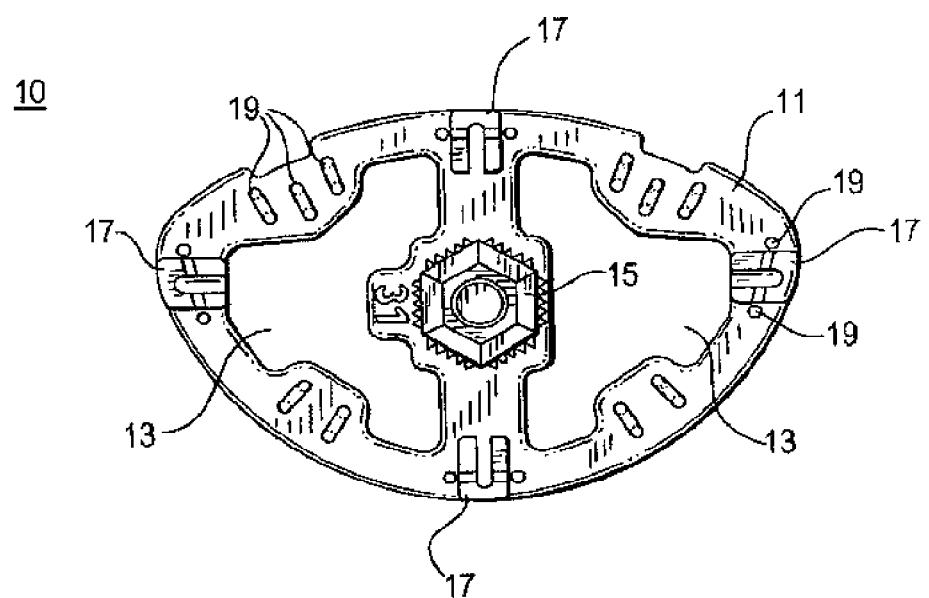
FIG. 2 is a top view of a planar annuloplasty ring holder similar to that shown in FIG. 1.
Figure 4A:
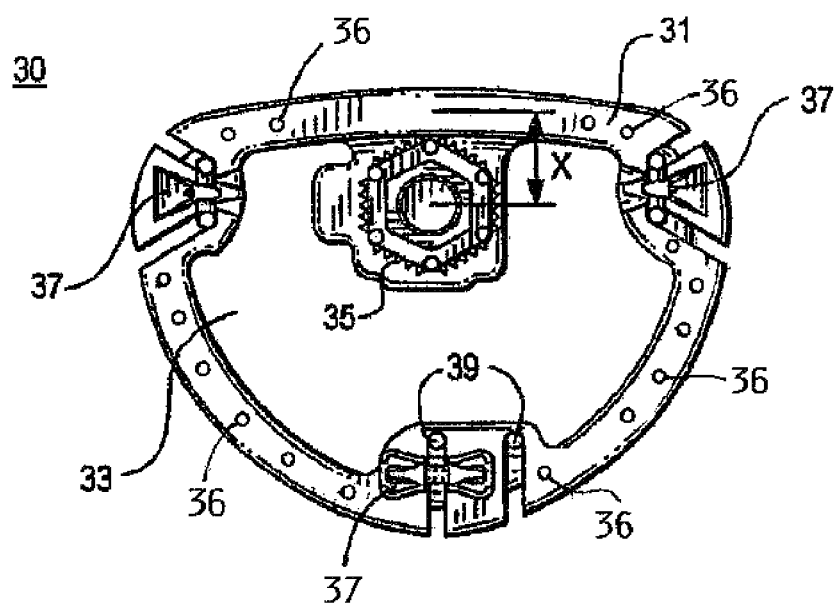
FIG. 4A is a similar view of a saddle-shaped annuloplasty ring holder as shown in FIG. 4, wherein the bracket includes additional apertures.
Figure 4:
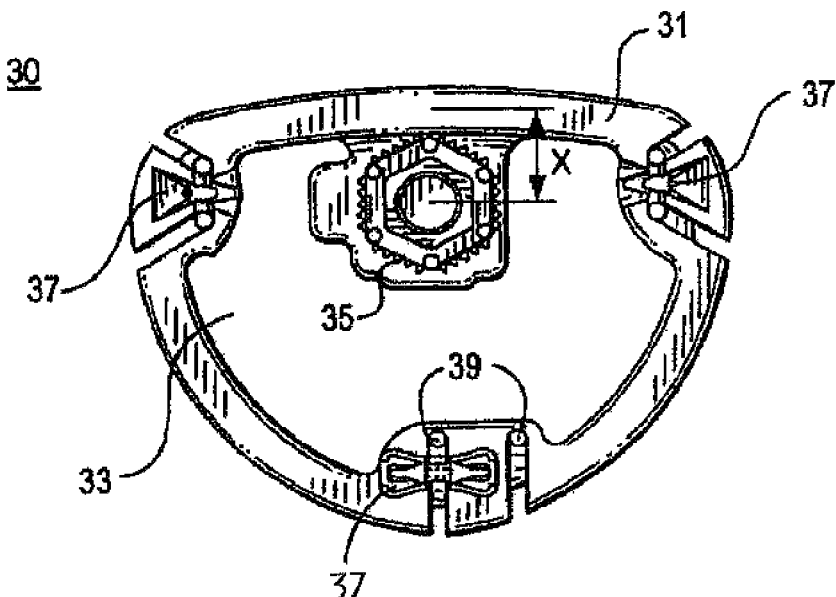
FIG. 4 is a top view of a saddle-shaped annuloplasty ring holder similar to that shown in FIG. 3.
Figure 5:
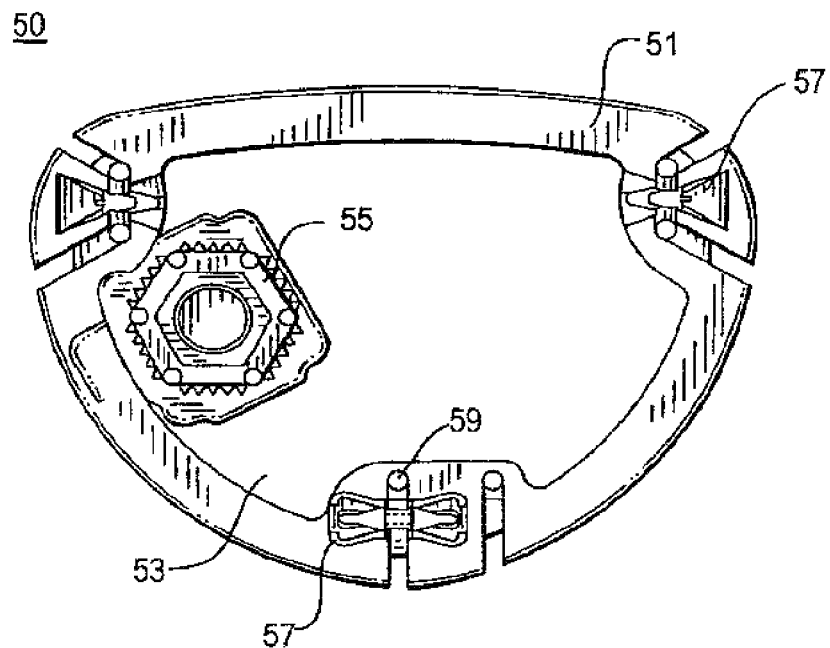
FIG. 5 is a top view of another illustrative annuloplasty ring holder in accordance with the invention.

FIGS. 2, 4, and 5 show top views of illustrative annuloplasty ring holders 10, 30, and 50. The upper surface of each holder is visible in these top-down views. The three holders 10, 30, and 50 include outer oval 11 or D-shaped 31 and 51 bracket structures which can support annuloplasty rings mounted on the holders. The shape of the bracket may be designed to approximate the shape of an associated annuloplasty ring. The bracket can have a portion of the upper surface forming an upper flange, and a lower, radially outwardly facing annular surface, where the lower annular surface has a height that extends from the upper flange to a lower-most point on the lower annular surface. The annular surface is engageable with an annuloplasty ring. The bracket may also be shaped according to other criteria. The bracket may also be made of flexible or semi-flexible material, and may adapt its shape to that of the ring it is supporting. The holders 10, 30, and 50 also include other features visible on their upper surface, including cutting blocks 17, 37, and 57, suture threading holes 19, 39, and 59, and connectors 15, 35, and 55. Each of these features will be discussed in more detail in following sections of this description.

The center of the annuloplasty ring holder 10, 30, or 50 may include one or multiple large open areas 13, 33, or 53. The open area may be formed by multiple holes 13 pierced through the upper surface of the holder, or by a single large central hole 33 or 53. The center of the holder is pierced so as to increase the visibility of the heart valve region through the ring holder, enabling the surgeon to more accurately place and suture the annuloplasty ring at the implant site.

The center of the holder may contain at least one connector 15, 35, or 55. The connector is represented by a hexagonal stub in the accompanying figures. The connector may be used to attach the holder to a handle or other grasping device used by the surgeon to grasp and manipulate the holder. The connector is typically located along the bracket 31 or 51, or in the central portion of the bracket 11 with support arms connecting it to the outer bracket. The connector may also be located elsewhere on the ring holder. In a preferred embodiment, the location of the connector is determined so as to be accessible to the surgeon, and to provide easy and skillful manipulation of the ring and holder when a handle or other device is attached to the connector. The location of the connector may also be determined so as to increase the visibility of the heart valve area to the physician, and to decrease the cluttering of the operating area. Other requirements may also influence the location of the connector on the annuloplasty ring holder. In the illustrative embodiments shown in FIGS. 2, 4, and 5, the connector 15, 35, or 55 is alternately located in the middle of the bracket 11, or placed along the edge of the bracket 31 or 51 so as to provide a continuous open area 33 or 53 in the center of the bracket. The connector may be centered along the central axis of the bracket 10 or 30, located at another location on the bracket 50. The connector may also be located along the edge of bracket 11, in the center of brackets 31 or 51, or at any other location on holders 10, 30, and 50.

Figure 3:
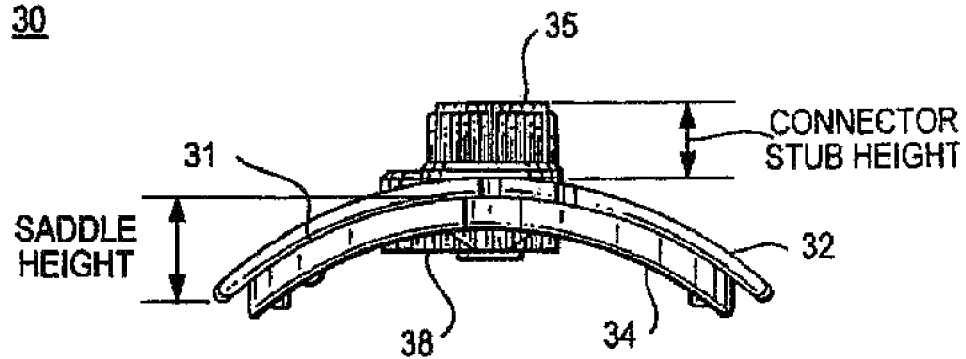
FIG. 3 is a side view of an illustrative saddle-shaped annuloplasty ring holder in accordance with the invention.

FIGS. 1 and 3 show side views of annuloplasty ring holders 10 and 30. The holder 10 may be planar, as shown in FIG. 1. A planar holder may have an essentially flat bracket 11. The holder 30 may alternatively be saddle-shaped, to more closely follow and support the shape of a saddle-shaped ring. A saddle-shaped ring holder may have a non-planar bracket 31, and may be used to secure and support essentially saddled-shaped annuloplasty rings. Saddle-shaped rings may more closely follow the natural shape of the base of the heart valve (e.g., the mitral valve), and may thus further improve the functioning of the valve after implantation of the ring. The saddle of the ring holder may be symmetrical on the posterior and anterior section of the holder. The saddle may have varying height, typically in the range of 2 mm to 10 mm from the lowest to highest points on the holder (corresponding to an Annular Height to Commissure Width Ratio (AHCWR) in the range from about 5% to about 25%).

Figure 6A:
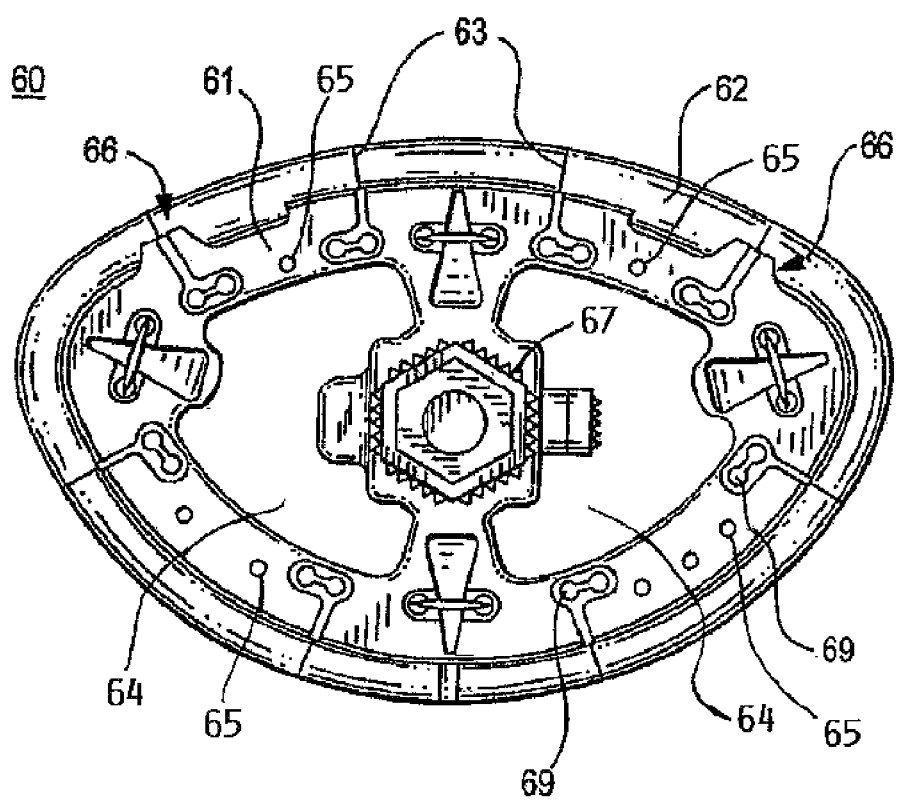
FIG. 6A is a top view of an illustrative annuloplasty ring holder attached to an annuloplasty ring, in accordance with the invention.
Figure 6:
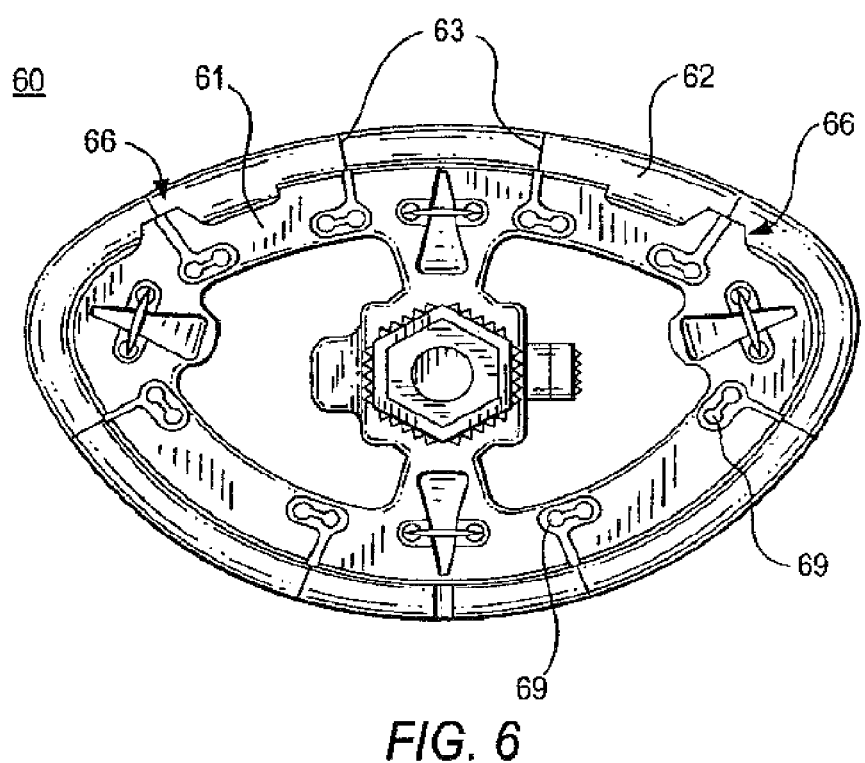
FIG. 6 is a top view of an illustrative annuloplasty ring holder attached to an annuloplasty ring, in accordance with the invention.

The ring holder may incorporate other features to aid the physician during the ring implantation procedure. FIG. 6 shows a ring holder 60 with indicator tabs 66. An annuloplasty ring 62 is shown attached to the ring holder 60. The indicator tabs 66 indicate the trigone locations, and help the physician to align the ring on the heart valve with ease and precision. The indicator tabs may be printed, molded, or other visual indications placed on the ring or ring holder, which help align the ring and holder on the heart valve. Indicator tabs may also assume other forms.

The annuloplasty ring 62 shown in FIG. 6 may be a full circular ring (as shown), a circular ring with a gap (a gapped ring), or a C-shaped prosthesis, among others. For simplicity, the term 'ring' is used herein to refer to any annuloplasty ring embodiment. Note that while either full circular or C-shaped rings are alternatively shown in the accompanying figures, the holders, features and embodiments described herein may be used with any type of ring, except in those cases where it is specified otherwise.

As noted above, the annuloplasty ring holder, for example holders 10, 30 and 50, can be rigid, semi-flexible, or flexible, and may alternatively be used during open-heart or minimally invasive surgery. The bracket 11, 31 and 51, of the ring holder can be rigid, flexible or semi-flexible. A flexible holder may be especially well-suited for minimally invasive surgery, wherein the chest incisions are so small that it can be difficult to introduce an annuloplasty ring into the body. To compensate for the difficulty of introducing a rigid or semi-rigid holder, the surgeon may remove the annuloplasty ring from the holder, thus losing the benefits of using a ring holder. In one aspect, a flexible holder with a flexible bracket can be compressed to pass through the port or small incision and then re-expanded when in the chest.

Further, a flexible holder can provide some tissue stress relief when the annuloplasty ring is being attached to a valve annulus. A diseased heart valve annulus may be very fragile, dependent upon the nature of the heart disease, and the diseased heart valve may not match the shape of the ring holder. When a surgeon places sutures through the fragile tissue of the annulus and then through the annuloplasty ring in order to tie the knots on the holder, the tissue is pulled toward the holder and increased stresses are placed on the tissue. A flexible holder, in this instance, would be more forgiving to the tissue when pulling the tissue to meet the ring on the holder, and the flexible holder could move toward the tissue to relieve some of the stress. Increased stress can lead to microscopic or gross tearing of the tissue and may contribute to ring dehiscence.

In one embodiment, the holders 10, 30, 50, 60 and 100, for example, can be flexible holders with flexible brackets 11, 31, 51, 61, and 101, respectively. The flexible holder can be constructed of at least two different durometer materials. A lower durometer material (more flexible, softer) can be used to construct the flexible bracket, and a higher durometer material (harder material) can be used to construct the connector structure. In one embodiment, the biocompatible material used for the flexible bracket 11, 31, 51, 61, or 101, can be selected from the group consisting of, but not limited to, thermoplastic elastomers generally, polyester, polyamide polyether block amides such as PEBAX® (low durometer) or VESTAMID®, polyurethanes and urethanes (for example, ELAST-EON™, PELLETHANE®, TECOTHANE®, BIONATE®, CARBOSIL®, PuriSil™), polyethylene, polybutylene, silicon, rubber, certain polyimide, nylon, and fluorinated hydrocarbon polymers, SANTOPRENE® thermoplastic vulcanizates, and the like. The material selected for the bracket 11, 31, 51, 61, or 101, is flexible and, in one embodiment, the durometer value can range from about 20 Shore A to about 100 Shore A. In another embodiment, the durometer value can range from about 35 Shore A to about 80 Shore A. In yet another embodiment, the durometer value can range from about 40 Shore A to about 70 Shore A.

Figure 2A:
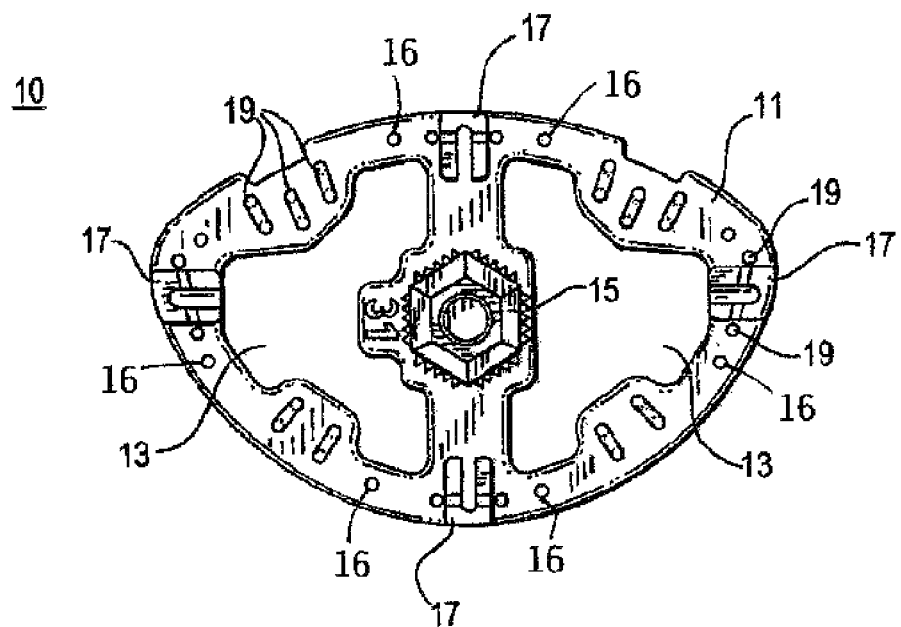
FIG. 2A is a view of a planar annuloplasty ring holder similar to that shown in FIG. 2, wherein the bracket of the ring holder includes additional apertures.
Figure 5A:
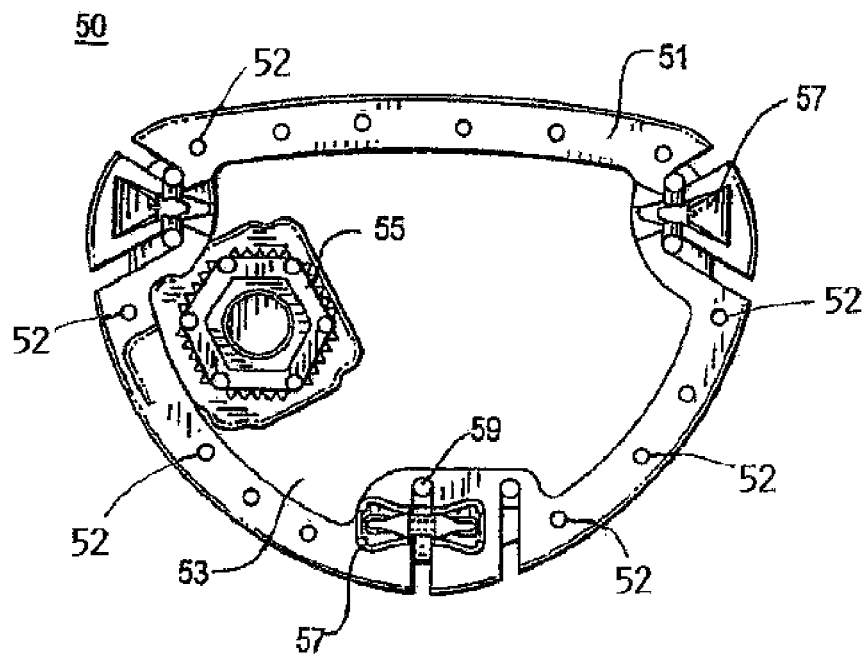
FIG. 5A is a top view of another illustrative annuloplasty ring holder in accordance with the invention.

Flexibility can be imparted to the bracket 11, 31, 51, 61, or 101 through the choice of material used to construct the bracket, as well as the configuration of the bracket 11, 31, 51, 61, or 101. For example, FIG. 2, FIG. 6, and FIG. 10 disclose holders 10, 60, and 100, respectively, with multiple suture threading holes 19, 109 or multiple suture channels 69. These threading holes and channels not only provide suture attachment points, but also allow the holder to flex and move in the localized area around the holes or channels. Should additional flexibility be required, apertures 16, 65, and 103, respectively, can be added to the brackets 11, 61, and 101, as shown in FIGS. 2A, 6A, and 10A. The number and pattern of the apertures 16, 65, and 103, can be arranged such that the structural integrity of the bracket is maintained. The holders shown in FIGS. 4A and 5A include apertures 36 and 52, respectively, in addition to the suture threading holes 39, 59. The apertures 36 and 52 are provided in the brackets 31 and 51 to enhance flexibility of the holder, especially in the area around the apertures 36, 52. Additional apertures 36, 52 can be added to the brackets 31, 51, as needed, and the pattern and placement of the apertures 36, 52 can be modified to provide the flexibility and performance characteristics desired. Further, the center of the ring holder 10, 30, 50, 60, 100, includes one or multiple large open areas 13, 33, 53, 64, 102, respectively. As noted above, the open areas increase the visibility of the heart valve region through the ring holder, enabling the surgeon to more accurately place and suture the annuloplasty ring at the implant site. However, the open area structure also provides the bracket 11, 31, 51, 61, and 101 with additional flexibility during annuloplasty ring implantation. Hence, the characteristics of the material used to construct the bracket 11, 31, 51, 61, and 101, and the configuration of the suture threading holes/channels, additional apertures, and open area in the center of the ring holder 10, 30, 50, 60, 100, can be combined in various ways to achieve the desired flexibility in the annuloplasty ring holder.

The connector 15, 35, 55, 67, 105, for example, as described in greater detail below, provides an attachment point for a handle or other grasping instrument, such as forceps, to the holder. The handle or grasping instrument can assist in providing improved manipulation of the holder and annuloplasty ring. If a handle is attached to the holder, it can be secured to the holder in a variety of ways, including using a snap fit, screw thread, twist pin or other means of connecting a handle. As noted above, the connector can be constructed of a higher durometer material, as compared to the material of the flexible bracket. The connector can be made of a more rigid biocompatible material including, but not limited to, stainless steel, cobalt, other metals and alloys, nitinol, acetal resin (such as DELRIN®), polysulfone, RADEL® polyphenylsulfones, titanium, ELGILOY® Co—Cr—Ni alloys, thermoplastics such as polyolefins, (e.g. ultra high molecular weight (UHMW)), polyesters, polyamides, acrylics, methacrylates (e.g. polymethyl methacrylate (PMMA)), polycarbonate, polyacrylontriles, polyaramides, PEEK (polyaryletheretherketone), PTFE (polytetrafluoroethylene), high durometer PEBAX®, ABS (acrylonitrile butadiene styrene), flexible materials with fiberglass/carbon reinforcement, to name a few example materials.

In one embodiment, a flexible holder can have a rigid connector, wherein the connector is made of higher durometer material than the holder bracket. The connector portion of the holder can be molded first, from the harder, higher durometer material. The connector can then be placed in the bracket mold and the lower durometer material can be molded in the mold cavity. The lower durometer material is overmolded onto specific portions of the rigid connector, thereby joining the connector and the bracket. In another embodiment, the connector and the bracket can be made of the same material, for example, using a higher durometer material for both the connector and the bracket, thus forming a rigid or semi-flexible holder.

As noted above, the annuloplasty ring can be secured to the holder, and particularly to the bracket, using a variety of means and methods including using suture threads to tie the ring to the holder. Other means and methods of securing the ring to the holder and releasing the ring from the holder are described below. In the instance of using suture threads to tie the annuloplasty ring to the holder, the ring can be released from the holder by cutting the suture threads using cutting blocks. Cutting blocks 107 are shown, for example, in FIG. 10, FIG. 10A and FIG. 11, and further details of the use of cutting blocks are provided below. Cutting blocks can be included in the structure of a rigid, semi-flexible or flexible holder. In one embodiment, similar material can be used in forming the bracket and the cutting block in a rigid or semi-flexible holder, the material being of sufficient durometer that a nick of the cutting block by a scalpel will not dislodge any material that could possibly enter the body.

Incorporating cutting block(s) in a flexible holder can require that at least a portion of the cutting block be made of a higher durometer material than the bracket. In one embodiment, the cutting block 107 and the connector 105 can be made of the same or similar material, given that the connector is generally rigid and made of a higher durometer material than the bracket. To fabricate a flexible holder with rigid cutting blocks 107 and a rigid connector 105, the connector 105 portion of the holder and the cutting blocks 107 can be molded first, from the harder, higher durometer material. The configuration of the cutting block 107 defines the cutting slit 104. The shape of the cutting slits 104 of the cutting blocks 107 can be an asymmetrical half-moon shape, the shape of a standard scalpel blade, or other convenient shape. The cutting block 107 defining the cutting slit 104 includes interior surfaces that define the width, length, and depth of the cutting slit 104. The connector 105 and the cutting block 107 can be placed in the bracket mold and the lower durometer material can be molded in the bracket mold cavity. The lower durometer material is overmolded onto specific portions of the rigid connector 105, thereby joining the connector and the bracket. The lower durometer material can encase the exterior surface of the cutting block 107, the cutting block 107 defining the cutting slit 104, and thus connect the cutting block 107, including the cutting slit 104, to the bracket. Alternatively, the cutting block 107 can include tabs, wherein the tabs are overmolded by the lower durometer material and thus the cutting block 107 is joined to the flexible bracket. FIG. 11A shows a cutting block 107, including the interior surface of the cutting block 108 defining the cutting slit 104, wherein the cutting block 107, including the interior surface of the cutting block 108, can be of a higher durometer material than the material of the bracket 101. Further, a cutting block that protrudes above the top surface of the bracket (e.g. 17 in FIG. 1) can have a lower portion that can be overmolded by the lower durometer material, and thus be joined to the flexible bracket. Other shapes and locations of cutting blocks, as shown in, for example, FIGS. 1, 4, and 5, can be joined to the bracket by techniques such as, but not limited to, overmolding or partially encasing a portion of the cutting block.

In another embodiment, the cutting block 107 can be made of the same material as the bracket 101, and can be molded as one piece, along with the bracket 101. Once the bracket 101, including the cutting blocks 107, is molded, a coating can be applied to the interior surface 108 of the cutting block 107. The coating can impart a harder surface, such that a scalpel traveling in the cutting slit 104 will not nick and dislodge any material that could possibly enter the body. The coating must be resistant to solubilization and provide the required hard surface. Further, the coating should be able to withstand sterilization, should be biocompatible, and should cure quickly. In addition, the coating should be relatively easy to apply. Coatings for the interior surface 108 of the cutting block 107 include cyanoacrylates and epoxies, in particular, two-part epoxy systems, urethanes, and the like. The cyanoacrylates can include n-butyl cyanoacrylates and 2-octyl cyanoacrylates. The cyanoacrylate can be the type using an accelerator or one where an accelerator is not required. Curing the cyanoacrylate coating can be accomplished at room temperature, with a heat cure, or with UV light. The choice of cyanoacrylate coating is dependent upon various factors, including the material of the bracket 101, material of the cutting block 107 and interior surface 108 of the cutting block 107, sterilization needs, hardness of the cured cyanoacrylate, cure method and time, ease of application, biocompatibility, and the like. Alternative to a cyanoacrylate coating, an epoxy can be used to coat the interior surface 108 of the cutting block 107. The epoxy can be heat cured, cured at room temperature, or cure upon combination of two parts of the epoxy system. The choice of an epoxy coating, or urethane or acrylic coating, would be based upon similar factors as those listed above in the discussion of cyanoacrylate coatings. Loctite® is a supplier of medical grade cyanoacrylates, epoxies, urethanes, and other adhesives and coatings, which could meet the requirements of use as a cutting block interior surface hard coating.

B. Connector Structure

The connector 15, 35, or 55, is a part of the holder which can be used to attach the holder to a handle or other grasping instrument (not shown). The physician may attach a handle or grasping instrument to the connector in order to manipulate the holder and ring assembly, and to place them at an implant or other appropriate site. As noted above, the connector may include features allowing it to be grasped using fingers, forceps, or other means, or secured using a snap fit, screw thread, twist pin or other means of connecting a handle. The connector may also include permanent attachments, in cases in which the holder and handle or grasping instrument are a single entity. In the figures, the connector is illustratively represented as a hexagonal stub. This does not preclude use of a different non-hexagonal connector.

As noted above, and as illustrated in FIGS. 2, 4, and 5, the location of the connector on the holder may be varied to suit a variety of objectives. The connector may be placed in such a way as to maximize the physician's visibility of the implanted ring, of the heart valve, and of the operative area surrounding these structures. The connector may also be placed in such a way as to maximize the physician's ability to place and otherwise manipulate the ring and holder with accuracy, to maximize the physician's access to the operative area, and to minimize cluttering of the operative region with the handle or grasping device used to manipulate the holder. Other objectives may also influence the positioning of the connector on the holder.

The position of the connector in the holder's horizontal plane was discussed above in the context of FIGS. 2, 4, and 5. The following paragraphs describe varying the position and height of the holder in the vertical direction.

Figure 7:
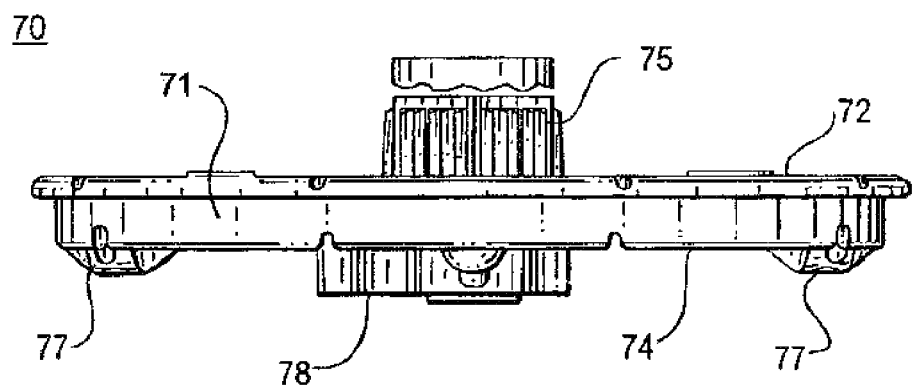
FIG. 7 is a side view of an illustrative planar annuloplasty ring holder with a shortened connector stub, recessed connector base and recessed cutting blocks, in accordance with the invention.

FIG. 1 shows a planar ring holder 10 with a connector 15 whose bottom surface is flush with the lower surface 14 of the holder. The connector stub 15 protrudes above the upper surface 12 of the holder, while the base of the connector is flush with the lower surface 14 of the holder. The planar ring holder 70 shown in FIG. 7 shows a recessed connector base 78 whose lower surface is lower than the lower surface 74 of the holder. The recessed connector base 78 may jut down below the holder bracket 71, jutting down into the valve orifice when the holder and ring are placed at the implant site. The ring holder 70 may also employ a shortened connector stub 75 which is shorter than a full-length connector structure 15 and protrudes less from the holder. In another embodiment, the connector base 78 may be further recessed into the holder 70, or the connector stub 75 further shortened, so as to reduce the protrusion of the connector structure from the ring holder 70. The shortening of the connector stub 75 and the lowering of the connector base provide better access and visibility along the upper portion of the holder. By reducing or eliminating the protrusion of the connector stub 75 above the bracket 71, the physician may have more space to tie the implanting suture knots, or to perform other manipulations along the periphery of the ring. The reduced protrusion of the stub 75 may also improve the physician's view of the periphery of the ring and other adjoining structures.

Figure 8:
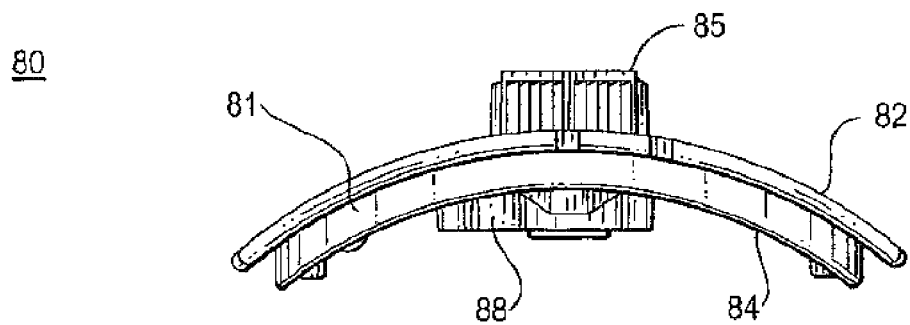
FIG. 8 is a side view of an illustrative saddle-shaped annuloplasty ring holder with a recessed connector base, in accordance with the invention.
Figure 9:
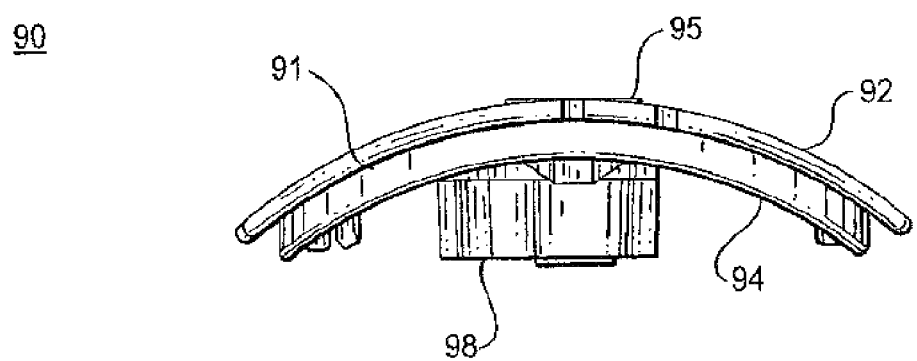
FIG. 9 is a side view of an illustrative saddle-shaped annuloplasty ring holder with a recessed connector base, in accordance with the invention.

FIGS. 8 and 9 show similarly recessed and shortened connectors 85 and 95 in the context of saddle-shaped ring holders. In a first embodiment 30 of a saddle-shaped holder shown in FIG. 3, the connector base 38 is approximately level with the highest point reached by the lower surface 34 of the holder bracket 31. The connector stub 35 protrudes above the highest point reached by the upper surface 32 of the bracket. In a second embodiment 80, the connector base 88 is lower than in the first embodiment 30. This causes the connector stub 85 to protrude less above the upper surface 82 of holder bracket 81, increasing visibility above the holder 80. Similarly, in a third embodiment 90, connector base 98 is further recessed. Connector stub 95 protrudes less above the upper surface 92 of bracket 91. In fact, in third embodiment 90, the connector stub 95 is almost flush with the upper surface 92 of the bracket 91. In both the second and third embodiments, the recessed connector stub bases 88 and 98 may jut down to varying degrees into the heart valve tissue and orifice found below the implantation site of the ring. In these second and third embodiments, the visibility of the operative area above the holders 80 and 90 is improved along the top of the holder by reducing the protrusion of connector stubs 85 and 95 above the holder brackets 81 and 91. Note that while shortened connector stubs such as stub 75 are not shown in FIGS. 3, 8, and 9, shortened connector stubs may be used in combination with saddle-shaped holders to reduce protrusion of the stub above the bracket. Shortened stubs may also be used to reduce the jutting out of connector bases 88 and 98 into the heart valve tissue below the bracket 81 and 91.

C. Cutting Blocks

Before and during the implantation procedure, the annuloplasty ring may be secured to the holder. The holder may be used to hold and manipulate the ring as it is placed at the implant site, and to support the ring during handling and while the ring is sutured into place. The holder may be detached from the ring during the implantation procedure, because the holder is typically not implanted with the annuloplasty ring into the heart. The ring may be secured to the holder using a variety of means. The ring may be attached to the holder using suture thread, or other thread-like structures. Alternatively, the ring may be attached to the holder using other releasable means. Various methods that may be used to secure the ring to the holder are described in more detail later in this specification.

In embodiments of this invention in which annuloplasty rings are secured to the ring holder by suture threads or other means amenable to cutting, cutting blocks may be included on the holder. Cutting blocks are guides used to facilitate the cutting of suture threads or other means of attaching an implanted annuloplasty ring to a holder. Cutting blocks may be used to help the physician locate the appropriate suture threads to cut, to ensure that the physician cuts the proper threads, and to prevent the physician from cutting tissue or sutures other than those passing through the cutting block.

Cutting blocks may include visual or other guides indicating to the physician the preferred location or locations where a suture thread used to attach the ring to the holder may be cut. In this way, cutting blocks may be used to identify those sutures that should or can be cut to release the ring from the holder. Cutting blocks may include painted, molded, or other visual indications highlighting the locations of preferred cutting locations. Cutting blocks may also include physical guides that direct or steer in other ways the physician to a preferred cutting location. In a preferred embodiment, the cutting blocks may include slots or other guiding means used to direct the physician's scalpel blade and ensure that the appropriate suture thread is cut.

Cutting blocks may be located at a variety of locations on the ring holder. In the particular embodiment shown in FIG. 10, four cutting blocks 107 are placed at various locations on the holding bracket 101. In the embodiment shown in FIG. 4, three cutting blocks 37 are located on bracket 31. Holders with more or fewer cutting blocks, or cutting blocks placed at different locations on the bracket or on the holder, may also be used. As in the case of connector locations, cutting blocks may be placed in the center of the bracket, if appropriate, with support structures holding the cutting block in place with respect to the bracket.

The location of cutting blocks may also be varied in the vertical holder plane. Cutting blocks, which include cutting slots, have non-negligible depths. Such cutting blocks may be thicker than the holder brackets 11, 31, or 71, and may protrude above or below the upper and lower surfaces of the brackets, respectively. As in the case of connectors, the vertical position of the cutting blocks may be varied to increase access and visibility around the upper edge of the holder, or to satisfy other objectives. FIG. 1 holder 10 shows cutting blocks 17 protruding above the upper surface 12 of bracket 11. The cutting block may be recessed, as shown in FIG. 7. In the holder embodiment of FIG. 7, cutting blocks 77 do not protrude above the upper surface 72 of bracket 71. Instead, cutting blocks 77 protrude below the lower surface 74 of bracket 71. Recessed cutting blocks 77 may protrude into the valve tissue and valve orifice found below the ring implantation site. However, recessed cutting blocks 77 provide better visibility along the upper surface 72 of holder 70, giving the physician an unobstructed view of the implanted ring and structures adjacent to the implant site. While recessed cutting blocks 77 are shown in FIG. 7 in the particular context of planar holder 70, recessed cutting blocks may be included on saddle-shaped holders, or other types of implant device holders.

Figure 10:
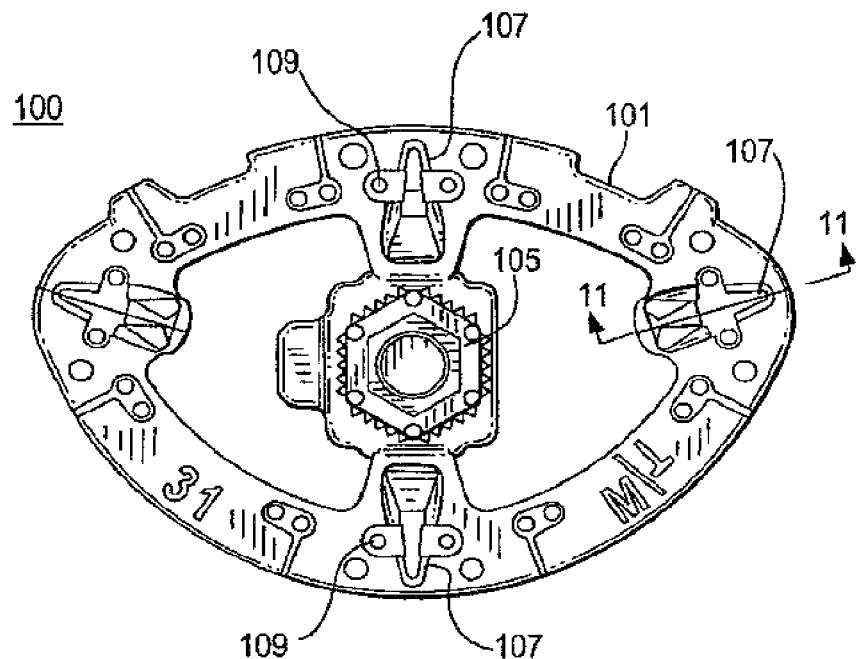
FIG. 10 is a top view of an illustrative planar annuloplasty ring holder indicating the location (at line 11-11) of the cross-sectional view shown in FIG. 11, in accordance with the invention.
Figure 11:
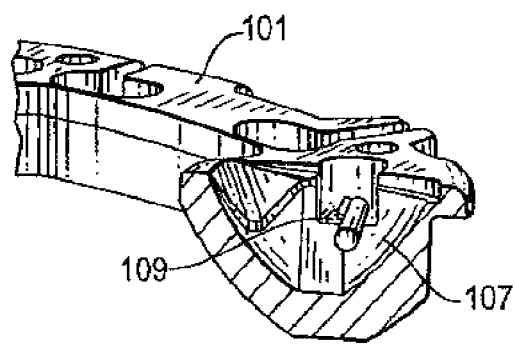
FIG. 11 is an oblique, cross-sectional view of a planar annuloplasty ring holder taken along the line 11-11 in FIG. 10, in accordance with the invention.
Figure 10A:
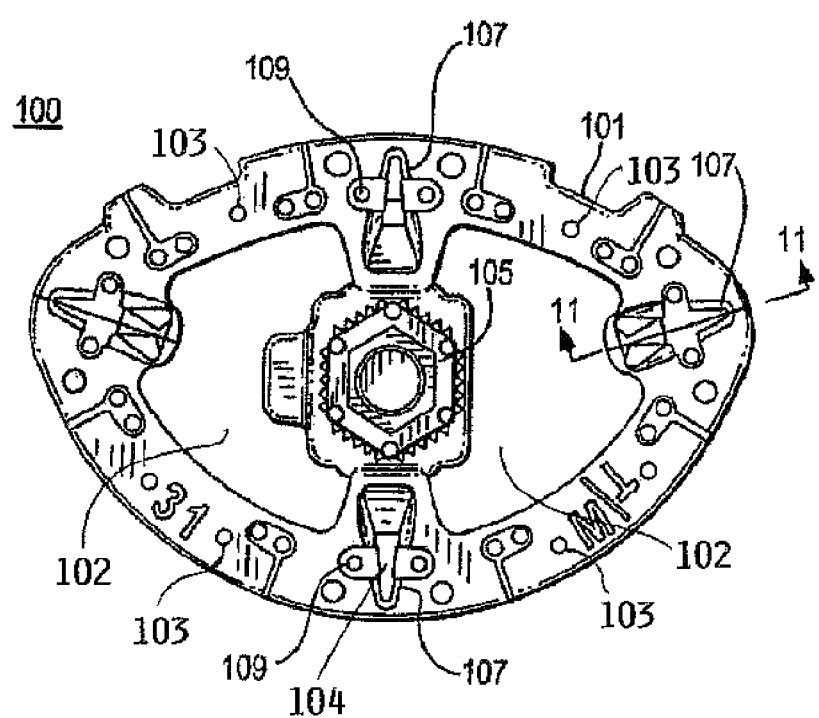
FIG. 10A is a top view of an illustrative planar annuloplasty ring holder in accordance with the invention.
Figure 11A:
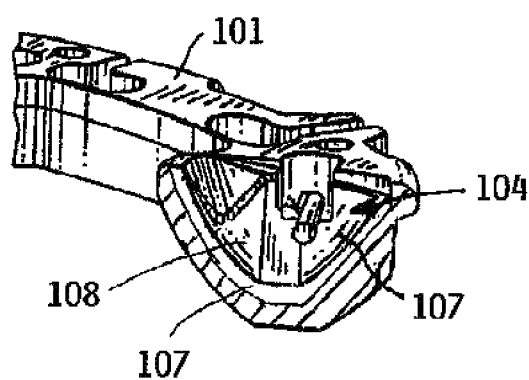
FIG. 11A is an oblique, cross-sectional view of a planar annuloplasty ring holder taken along the line 11-11 in FIG. 10, in accordance with the invention.

FIGS. 10 and 11-11A show two views of an illustrative annuloplasty ring holder that includes cutting blocks. FIG. 10 shows a top-down view of a holder 100, showing the plane of section 11-11 illustrated in the cross-sectional view of FIG. 11. The cross-sectional view of FIG. 11 shows a cut-away view through a cutting block. As seen in FIG. 11, each cutting block 107 may include a slit 104 into which a scalpel blade may be introduced, and two holes 109 through which suture thread may pass. The axis of the holes intersects the axis of the cutting slit 104, so that a thread passing through the holes crosses the cutting slit 104. The thread may cross at approximately half the slot depth. When a scalpel is passed through the cutting slit 104, the suture thread is cut, releasing at least one section of the ring from the holder.

The cutting slit 104 shown in cross-sectional view 11-11 of cutting block 107 may have an asymmetrical half-moon shape. The cutting slit 104 may be shaped to match the shape of the scalpel blade, in order to increase cutting efficiency. The shape of the slit 104 may also be designed to guide cutting in a preferred direction, or to permit cutting in both directions. The shape may also be adjusted to draw the cutting action upward and away from the tissue, minimizing the risk of damaging structures surrounding the implant site. In the particular example shown in FIG. 11-11A, the cutting slit 104 may match the shape of a #15 scalpel blade. Slits may be shaped to match other standard scalpel blades.

Figure 12A:
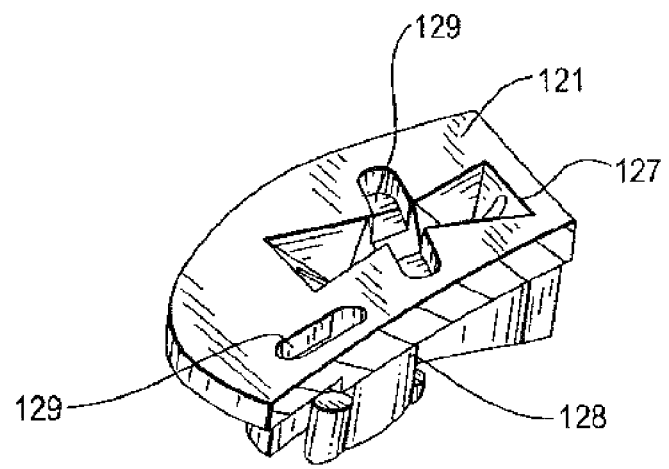
FIGS. 12a-12c are a series of three cut-away views of an illustrative annuloplasty ring holder including knot tying posts in accordance with the invention.
Figure 12B:
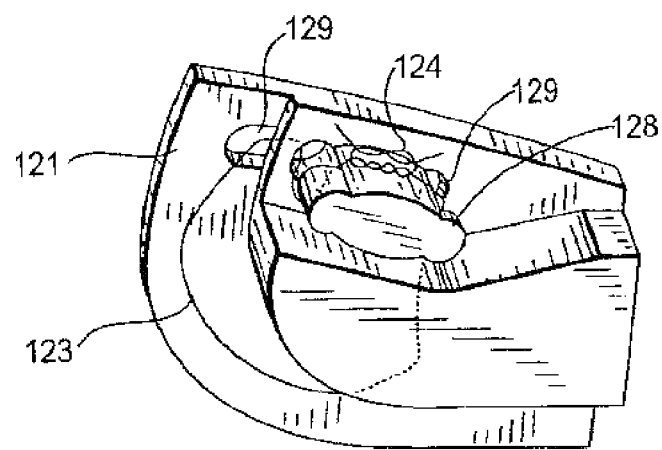
Figure 12C:
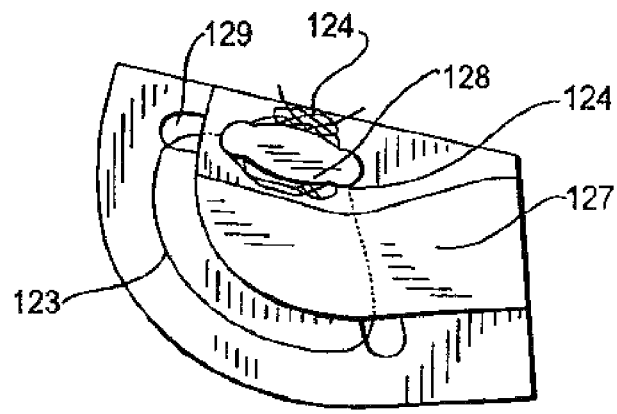

Annuloplasty ring holders may include knot tying posts on which suture threads used to hold the ring to the holder may be knotted. The knot tying posts may be placed next to cutting blocks, as the suture thread may pass through both structures. As shown in FIGS. 12a-12c, the thread 123 may pass through the annuloplasty ring and the cutting block's suture channels 129, and have at least one of its ends knotted 124 to a knot tying post 128. Both ends of the thread may also be knotted 124 to each other and to the knot tying post 128, as shown in FIGS. 12a-12c. The knot tying post may be used to hide sutures used to hold the ring to the holder underneath the holder's upper surface. As such, knot tying posts may be located on the lower side of the holder, so as to reduce visual distractions on the holder's upper surface. The knot tying post may also be used to ensure the suture thread does not remain attached to the implanted annuloplasty ring after the ring is released from the holder. To this end, both ends of the suture thread may be tied to a knot tying post, thereby ensuring that both portions of the cut thread remain attached to the holder when the holder is removed from the implant site. Knots 124 may be tied on each side of the post, as shown on knot tying post 128, to retain the suture after it is cut.

D. Fixation of the Annuloplasty Ring to the Holder

Various methods may be used to secure the annuloplasty ring to the ring holder. Methods involving suture thread, or other thread-like implements, may be used to tie the ring to the holder. Alternatively, other retaining means may be used to secure the ring to the holder. These may include clamping devices or other restraining devices incorporated into the holder. Such devices are described in further detail in the following two sections of this description.

1. Suture Methods—Attachment to Holder

The annuloplasty ring may be attached to the ring holder using suture thread, or similar thread-like implements. The suture thread may pass through the holder, may be looped around the holder, or may be attached to the holder in other ways. FIG. 6 shows an exemplary arrangement in which the thread 63 passes through suture channels 69 on the holder bracket 61. The suture channels 69 may be located at various locations on the holder 60, in order to ensure that the ring 62 can be held firmly against the holder bracket 61. In the particular embodiment shown in FIG. 6, a single length of suture thread 63 may be looped multiple times through the holder 60 and around the ring 62. By looping the thread around the ring and holder assembly multiple times, fewer threads may be needed to hold the ring attached to the holder, because each length of thread secures the ring on the holder in multiple locations. In such an embodiment, fewer cutting blocks may be required because each length of thread need only be cut in one location. In the particular embodiment of FIG. 6, the ring 62 is retained by the thread 63 using forces pulling inward in the radial direction. The overhang of the holder bracket may therefore be reduced, improving access to the ring periphery and to the surgeon's suturing positions on the ring.

The suture thread may also be looped around the holder, with or without passing through suture channels on the holder. Such an embodiment is shown for example in FIGS. 14a and 14b. In this embodiment, the suture thread 143 may not pass through the holder bracket 141. Instead, the threads may be held taut against the edges of the bracket. Different means of wrapping the suture thread around the holder and bracket may be used. For example, means similar to those used to secure the ring described in the following section may also be used to secure the suture thread to the holder.

2. Suture Methods—Attachment to Annuloplasty Ring

In embodiments in which suture thread is used to secure the ring to the holder, the suture thread may be secured to the annuloplasty ring by passing through the ring, by looping around the ring, or by holding the ring to the holder in other ways. In one illustrative embodiment shown in FIG. 13a, the thread 133 may be passed one or more times through the ring 131 in a through stitch. The same thread may also pass through or wrap around the ring holder 132, as described in previous sections of this description.

Figure 13C:
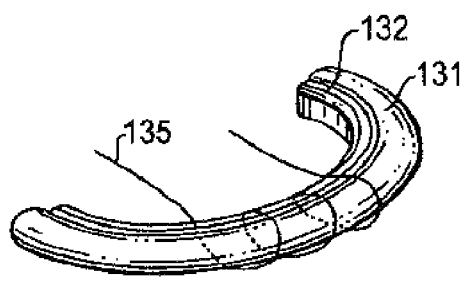
FIGS. 13a-13c show three illustrative suture thread wrapping methods in accordance with the invention.
Figure 13A:
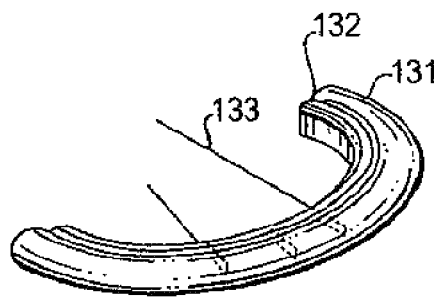
Figure 13B:
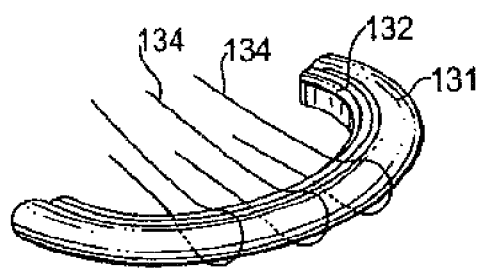

The thread may also wrap around the annuloplasty ring 131, with or without being stitched through the ring. FIG. 13b shows a thread 134 looping a single time around the ring 131 in one embodiment, and FIG. 13c shows a thread 135 wrapped multiple times around the ring 131 in a second embodiment. By wrapping the thread 135 multiple times around the ring and holder, a single length of thread can be used to secure a wider section of the ring against the holder than a single loop 134 of thread can secure. Wrapping the thread 135 multiple times around the ring and holder may reduce the total number of threads, cutting blocks, tying posts and other holder structures that may be used to hold the ring attached to the holder. By looping or wrapping the thread around the ring, the thread may pull the ring radially inward against the holder bracket. In such an embodiment, the holder bracket can have minimal overhang above and below the ring, supplying instead an inner support structure against which the ring is held. This may improve access to the ring's outer periphery, improving the physician's view and access to the ring periphery. Alternatively, the looping or wrapping of the thread around the ring can be used to pull the ring upward against a holder bracket placed substantially around the ring's upper surface. Such a holder may have fewer bracket structures in its center, providing the physician with an unobstructed view of the heart valve region through the center of the holder.

Figure 14A:
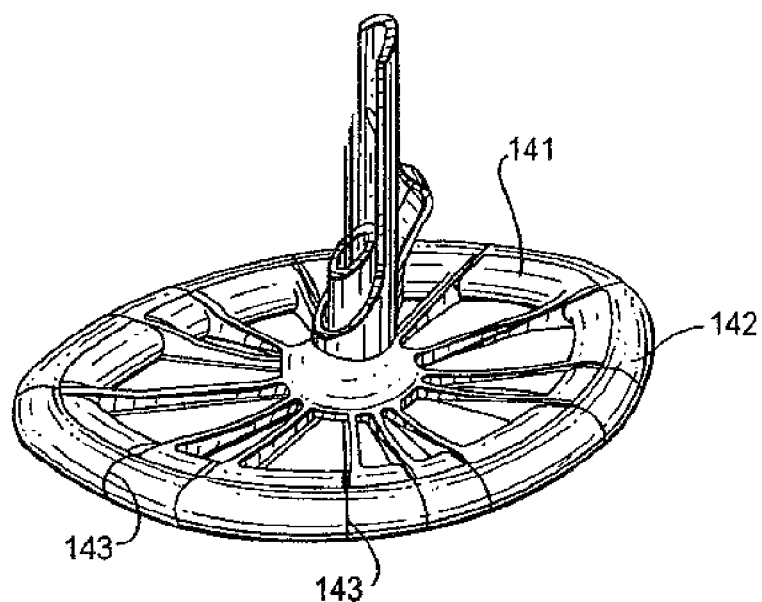
FIGS. 14a and 14b show an illustrative annuloplasty ring holder with releasable suture threads in accordance with the invention.
Figure 14B:
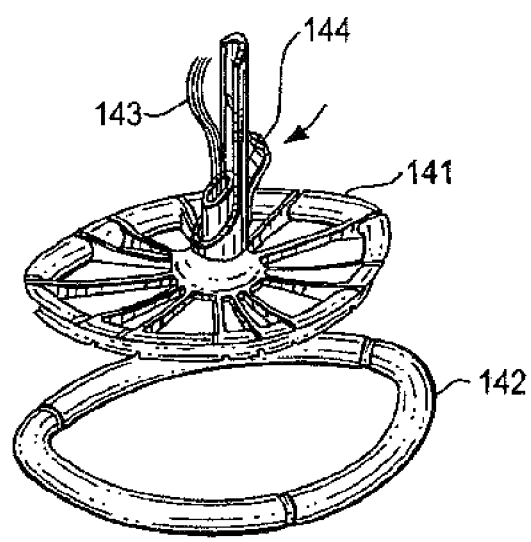

In embodiments in which suture methods are used to secure the ring to the holder, the thread or threads used to secure the ring may be cut to release the ring from the holder. The cutting may be performed using a scalpel, cutting blocks, or other appropriate cutting methods. Other methods may also be used to release the ring from the holder. FIGS. 14a and 14b show a push-button release method for disengaging the thread 143 and releasing the ring 142. The push-button 144 may be used to release one or multiple threads concurrently. Releasing of the ring may require one or multiple push-buttons to be pressed.

3. Non-Suture Methods

Other methods may be used to secure the ring to the holder. These methods may use internal tension, clamping, or other means to hold the ring.

FIGS. 15 through 20 show a series of illustrative holders that use internal tension or internal clamping to hold the ring. These holders may have braces that can extend or retract in the radial direction. When the braces are extended outwards, friction or internal tension forces between the brace and the ring may secure the ring to the holder. Alternatively, or in addition to internal tension, brace structures may be used to hold the ring.

Figure 15:
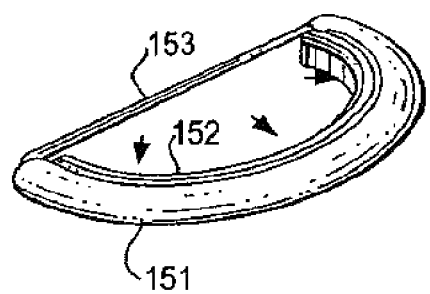
FIG. 15 is a schematic depiction of an illustrative internal tension annuloplasty ring holder in accordance with the invention.

FIG. 15 shows a basic internal tension holder 152 holding ring 151. Holder 152 may be stiff or elastic, and may include central structures to maintain its shape and elasticity, or to attach a connector. A flexible or semi-flexible holder 152 may be used to support D-shaped rings. In such a case, the natural shape adopted by the holder and ring assembly when internal tension is applied may be a saddle-shape. In general, ring 151 may be a complete annuloplasty ring. Ring 151 may also be a C-shaped (as shown) or gapped ring, which may require a stiff or elastic suture thread 153 to be tied between the ends of the ring. Suture thread 153 may serve to maintain the ring's shape, and to keep the ring on the holder. Holder 152 may be a flexible holder.

Figure 16A:
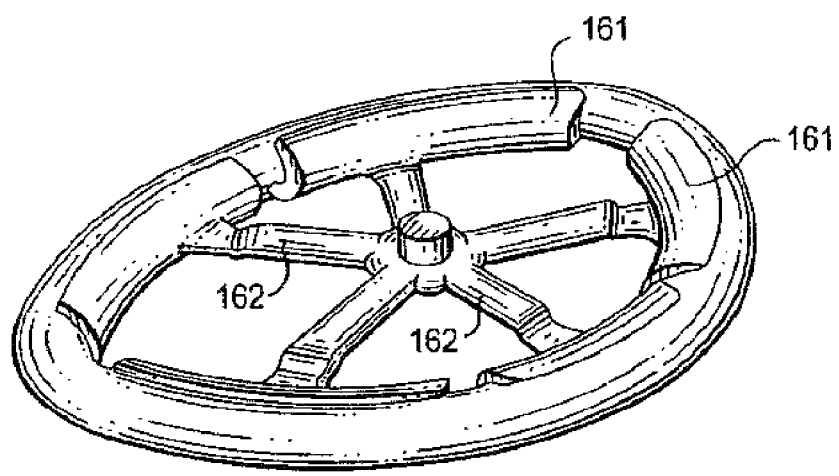
FIGS. 16a and 16b are two views of an illustrative internal clamping annuloplasty ring holder in accordance with the invention.
Figure 16B:
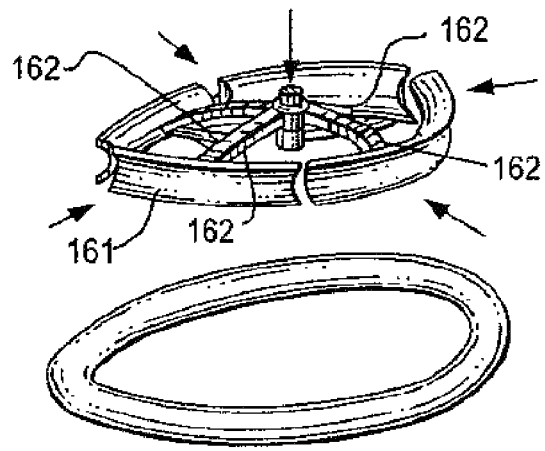
Figure 17A:
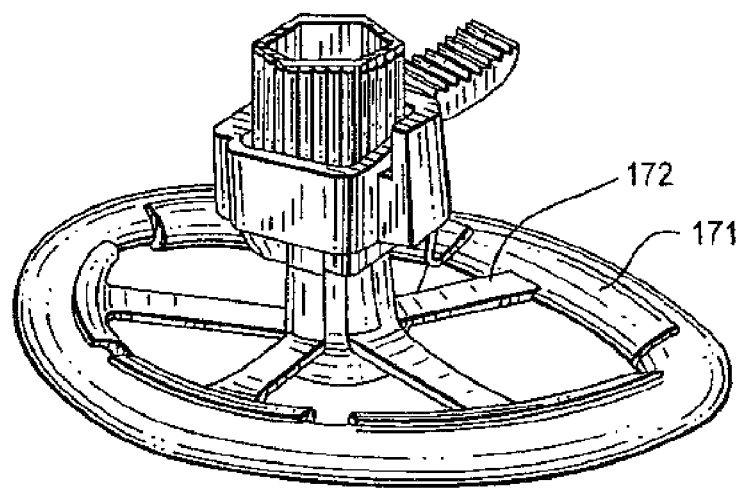
FIGS. 17a and 17b are two views of an illustrative internal clamping annuloplasty ring holder in accordance with the invention.
Figure 17B:
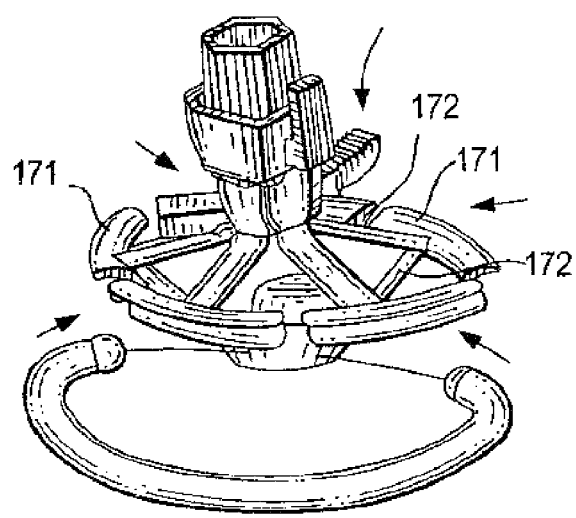
Figure 18:
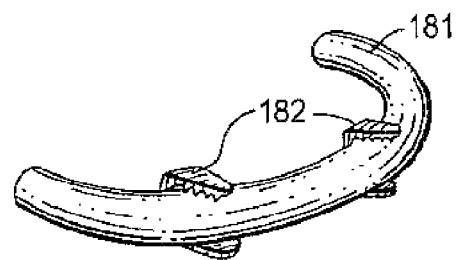
FIG. 18 is a schematic depiction of serrated clamps that may be included in an annuloplasty ring holder in accordance with the invention.

FIGS. 16 and 17 show holders with C-shaped braces 161 and 171. The beveled edges of the braces may serve to support the ring, and to keep it from slipping out of the holder when the braces are extended radially outward. Serrated, high friction, or clipping brackets may also be used to further secure the ring in the brackets. FIG. 18 shows one schematic embodiment of serrated clip brackets 182 holding ring 181. The clip brackets may have hinged jaws that can alternately clamp and hold the ring, or open and release the ring from the holder.

The holders may also have a release mechanism used to disengage the braces securing the ring. The release mechanisms may include a push-button or other type of mechanism which may be used to draw the braces inward, releasing the ring from the holder. FIGS. 16 and 17 show two exemplary release mechanisms in which a push-button or lever placed at or near the center of the holder is used to retract the braces. The release mechanisms shown in these figures are exemplary, and other known types of release mechanisms may be used in these holders. The braces may be retracted by moving upper and lower sets of radial bracket support arms 162 and 172 in substantially opposite directions. The upper set of support arms 162 or 172 may move substantially in an upwards direction, while the lower set of support arms 162 or 172 may move substantially in a downward direction. Movement of the support arms in different directions may act to draw retaining braces 161 and 171 radially inward, and to release the ring from the holder.

Figure 19A:
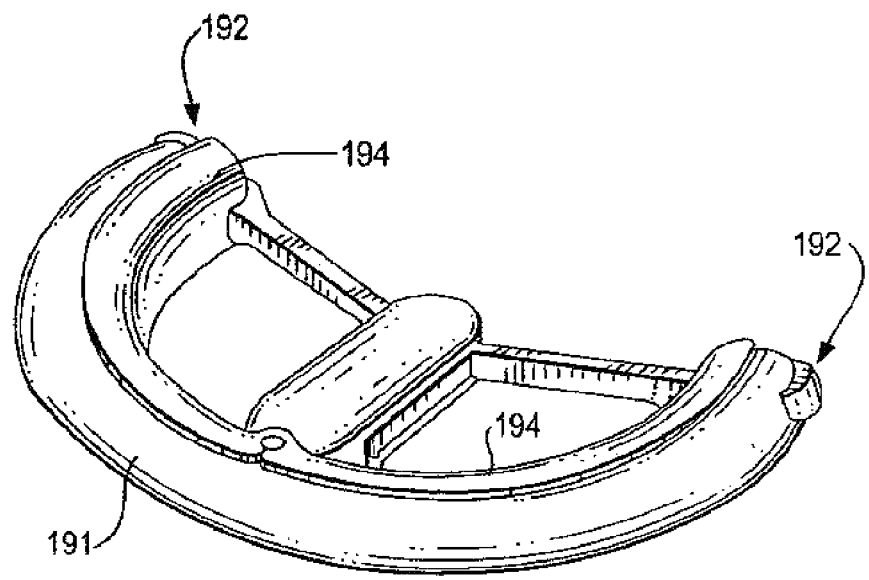
FIGS. 19a and 19b show an illustrative end-clamping annuloplasty ring holder in accordance with the invention.
Figure 19B:
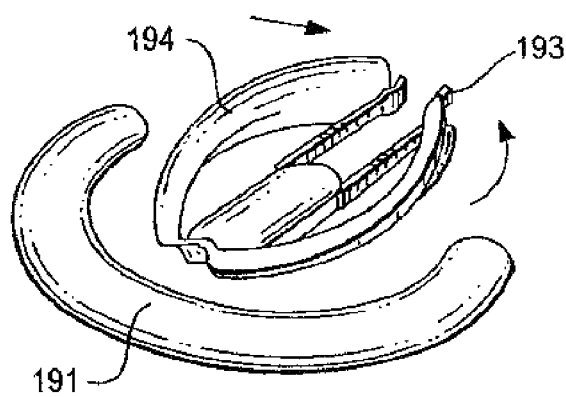

FIGS. 19a and 19b show an exemplary holder that uses end-clamps 192 to hold a C-shaped prosthesis ("ring") to the holder. The end-clamps 192 latch onto the ring 191, while beveled edges on the bracket may assist in securing the ring. The end-clamps may be disengaged as shown at 193 when the ring is released from the holder. A C-shaped holder may fold onto itself, as shown in FIG. 19b, to release the ring 191 from its outer brackets 194.

Figure 20A:
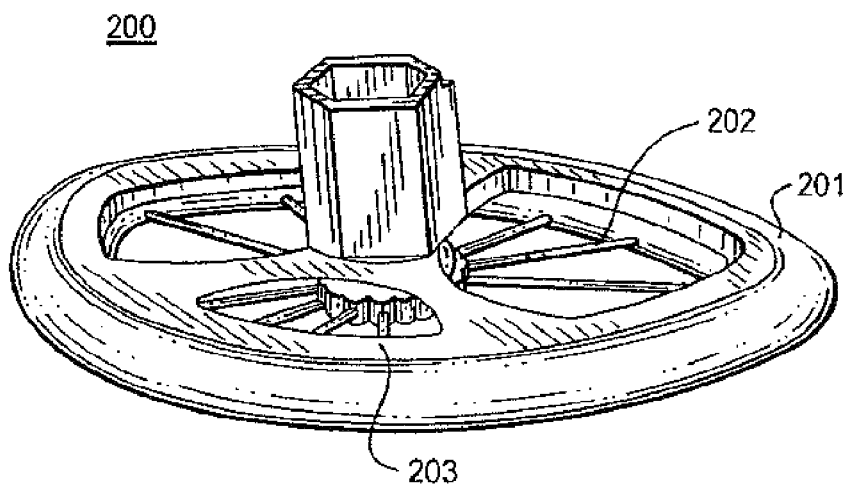
FIGS. 20a and 20b show an illustrative internal tension annuloplasty ring holder with retractable pins in accordance with the invention.
Figure 20B:
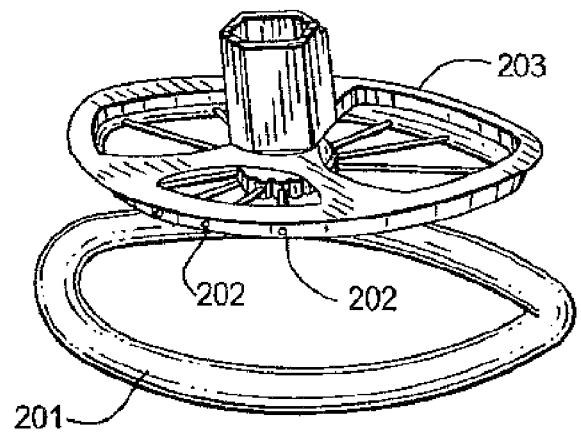

FIGS. 20a and 20b show an exemplary holder 200 that has retractable rods or pins 202 sticking radially out of a central holder structure 203. The rods or pins may be made of stiff or flexible materials, and may be made of shape memory alloy or nitinol. When engaged, the rods 202 extend radially outward from the central structure 203 and exert pressure at multiple points on the ring's inner surface. When disengaged, the rods 202 retract inward and release the ring 201 from the holder 200. The rods may be disengaged by rotating a central hub 203 into which the rods 202 are inserted. Other disengagement mechanisms may also be used.

Figure 21:
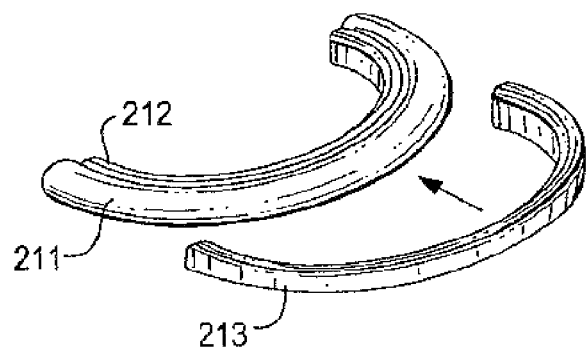
FIG. 21 is a schematic depiction of illustrative clamping brackets that may be included in an annuloplasty ring holder in accordance with the invention.
Figure 22A:
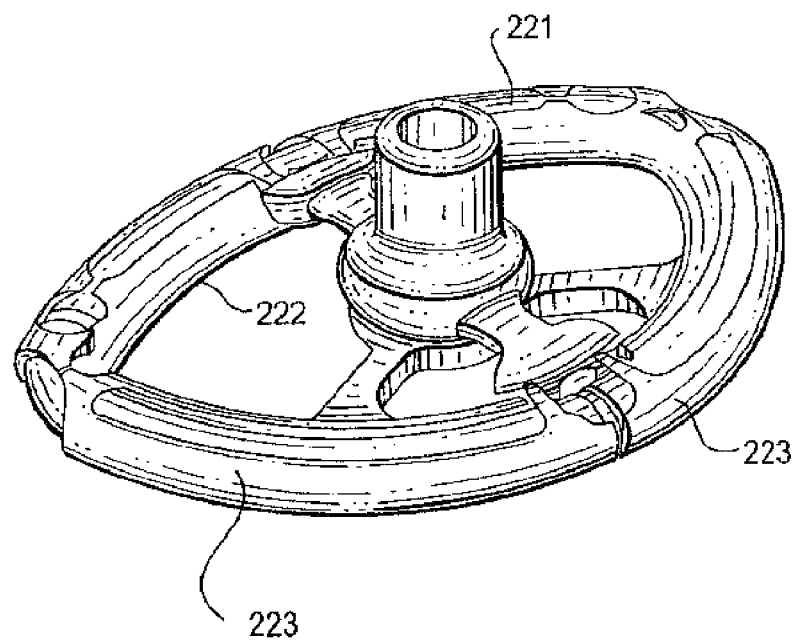
FIGS. 22a and 22b show an illustrative clamping annuloplasty ring holder in accordance with the invention.
Figure 22B:
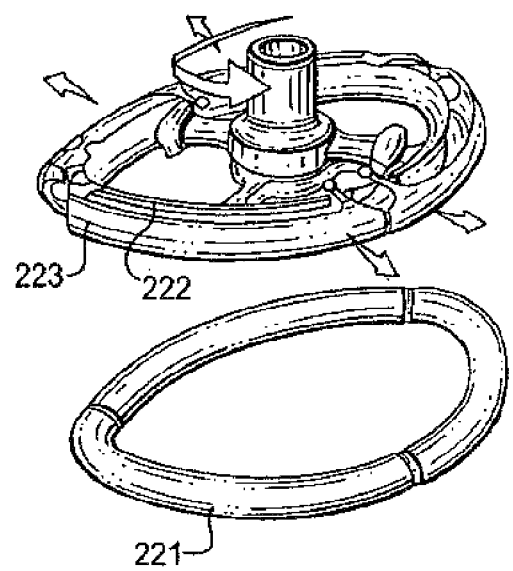

FIGS. 21 and 22 show clamping or clamshell holders. These holders may include one or more central braces 212 or 222, as well as one or more retractable outer supports 213 or 223. The central and outer braces may be used to substantially clamp or restrain the ring 211 or 221 in one or more locations around the ring. The braces may have beveled edges or protrusions to inhibit the ring from slipping out of the clamp. The clamping brace may release the ring by moving the inner and outer clamping braces apart. In one embodiment shown in FIGS. 22a and 22b, the outer braces 223 may be released, while the inner braces 222 may remain substantially stationary. In another embodiment, the outer braces may remain substantially stationary while the inner braces retract. Alternatively, both the inner and outer braces may move. The holder may release the ring using a push-button mechanism, or other mechanisms. In the particular embodiment shown in FIGS. 22a and 22b, the ring is released from the holder by applying a twisting action of a central portion of the holder, and disengaging the outer clamping or clamshell structures 223. The outer clamping or clamshell structures 223, once disengaged, may move freely and release the ring 221. Other known release and clamping mechanisms may also be used.

Figure 23A:
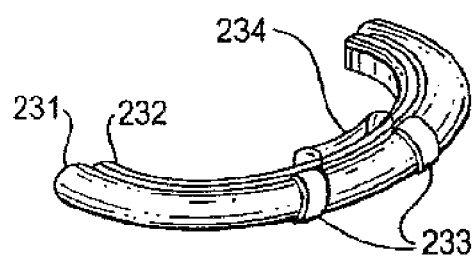
FIGS. 23a and 23b respectively show schematic depictions of an illustrative clamping annuloplasty ring holder and an illustrative non-thread holder in accordance with the invention.
Figure 23B:
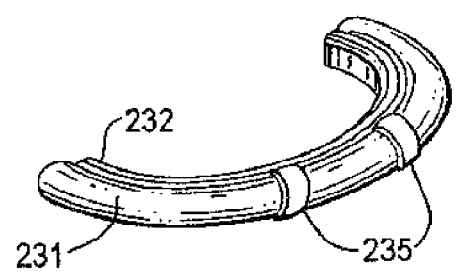

Clamping and other methods used to secure the ring into the holder may be combined with other retaining means. FIG. 23a shows ring 231 secured to holder 232 using clamp-like structures 233. Clamp-like structures 233 may comprise a variety of materials including thread, cloth, metallic, and/or plastic, among others. The clamp-like structure 233 may be held in place by suture thread 234. Clamp-like structure 233 may be released by cutting suture thread 234. FIG. 23b shows ring 231 secured to holder 232 using a non-thread wrap 235. Non-thread wrap 235 may be of any of a variety of materials, and may be wrapped around either or both of ring 231 and holder 232. As previously described in the context of suture thread holders, non-thread wrap 235 may be wrapped a single time around ring 231 and/or holder 232, or looped multiple times around either or both structures.

Figure 24:
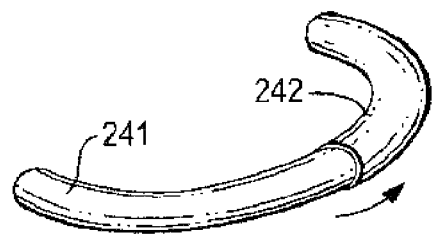
FIG. 24 is a schematic depiction of an illustrative sheath holder in accordance with the invention.

Other holder architectures may also be used. FIG. 24 shows a sheath holder including a tube structure 242 which fits around annuloplasty ring 241, and which can slide on and off of annuloplasty ring 241. The sheath holder may be used with either a C-shaped ring or a gapped full-ring, a gap being required to allow the sheath holder to be removed from the ring. Tube structure 242 may be rigid, to help maintain the shape of the ring. Alternatively, tube structure 242 may be flexible or unshaped. Such a flexible holder may be especially useful in minimally invasive surgery, in which the annuloplasty ring and holder may have to be implanted through an implantation catheter. A flexible holder may permit the physician to collapse the ring and holder into the implantation catheter, in order to bring them to the implantation site. The ring and holder assembly may regain its shape once withdrawn from the implantation catheter at or near the implantation site. During implantation of a ring mounted in a sheath holder, the ring may have to be withdrawn from the holder before suturing the ring at its implant site. The suturing may be done after removal of the holder. The suturing may also be done as the sheath holder is withdrawn, so as to keep unsutured portions of the ring secured and supported in the holder while sutures are tied to exposed portions of the ring.

E. Pre-Stitched Sutures

Figure 25A:
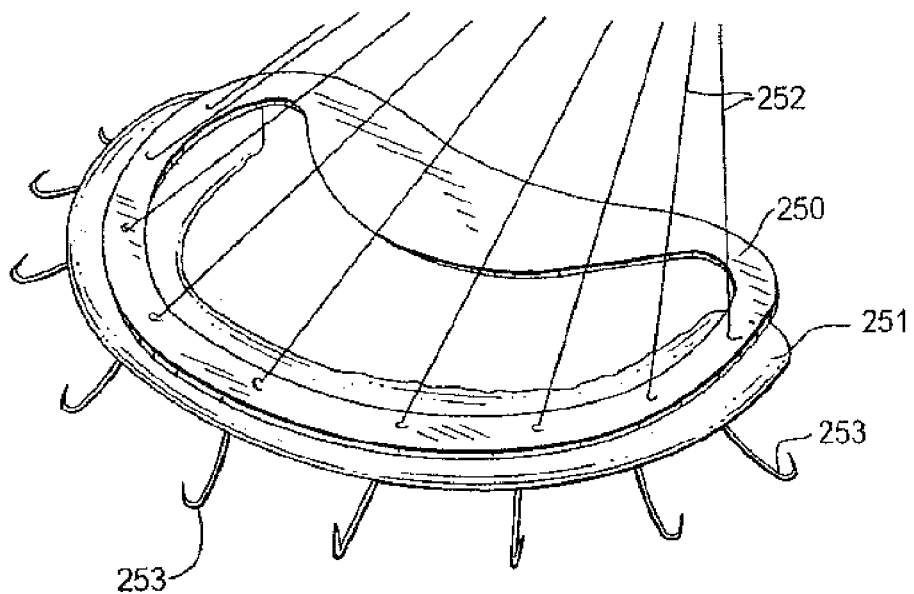
FIGS. 25a and 25b show an illustrative annuloplasty holder and ring with pre-stitched sutures in accordance with the invention.
Figure 25B:
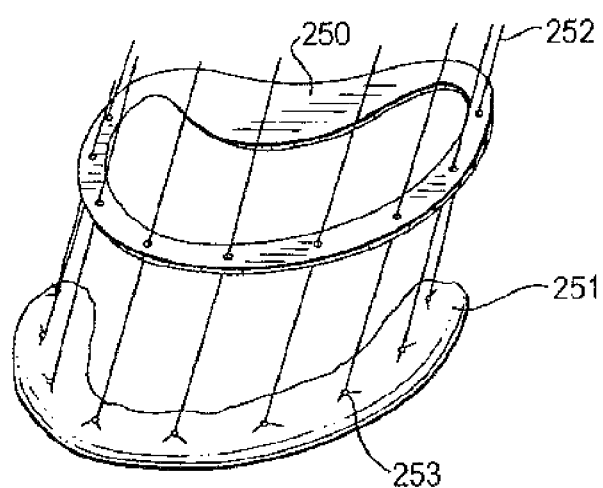

Annuloplasty rings mounted on holders such as the holders described herein may be mounted with pre-stitched sutures. FIG. 25a shows ring 251 attached to holder 250, with pre-stitched suture threads 252 extending from suture needles 253 through ring 251. The use of pre-stitched sutures 252 and needles 253 may facilitate and accelerate the suturing of the ring at the implant site. Their use may also allow for better alignment and spacing of the sutures, ensuring better placement of the ring. Anti-entanglement features may be incorporated with the pre-stitched sutures. Suture threads 252 may pass through holder 250, or may be used to secure or hold ring 251 to holder 250. Suture threads 252 may also not pass through holder 250, and may not be used to secure ring 251 to holder 250. FIG. 25b shows ring 251 sutured at the implant site by sutures 253. Sutures 253 may be tied while ring 251 is still attached to holder 250, or after the holder is removed from the ring.

The preceding description has been presented only to illustrate and describe exemplary embodiments of the invention. It is not intended to be exhaustive or to limit the invention to any precise form disclosed. Many modifications and variations are possible in light of the above teaching. Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents.

The invention claimed is:

1. A tool for holding and supporting an annuloplasty ring comprising:
  a flexible bracket having an upper surface, a central portion, and an outer bracket portion, a portion of the upper surface forming an upper flange, the outer bracket portion including a radially outwardly facing annular surface disposed below the upper flange and adapted to receive the annuloplasty ring thereabout, the annular surface having a height that extends from the upper flange to a lower-most point on the annular surface, the flexible bracket being formed from a material having a first durometer hardness; and
  a rigid connector attached to the flexible bracket, the connector defining a recess therein for attachment of a grasping device, the connector being formed of a material having a second durometer hardness higher than the first durometer hardness; and
  at least one cutting block positioned in the upper surface of the bracket, the at least one cutting block defining a slit, the slit configured to match a shape of a scalpel blade and to orient the scalpel blade in a plane that is transverse to a closest adjacent portion of a mounted annuloplasty ring, the at least one cutting block further comprising an interior surface, the interior surface comprising a coating, the coating being rigid and being formed of a material having a third durometer hardness higher than the first durometer hardness.

2. The tool of claim 1, the upper surface of the flexible bracket defining a plurality of apertures.

3. The tool of claim 1, wherein the material having the first durometer hardness is overmolded onto portions of the connector, thereby joining the connector and the bracket.

4. The tool of claim 1, the slit shaped to draw a cutting action of a scalpel traversing the slit substantially away from tissue surrounding the at least one cutting block.

5. The tool of claim 1, the coating selected from the group consisting of cyanoacrylates, acrylics, urethanes, and epoxies.

6. A tool for holding and supporting an annuloplasty ring comprising:
  a flexible bracket having an upper surface, a central portion, and an outer bracket portion, a portion of the upper surface forming an upper flange, the outer bracket portion including a radially outwardly facing annular surface disposed below the upper flange and adapted to receive the annuloplasty ring thereabout, the annular surface having a height that extends from the upper flange to a lower-most point on the annular surface, the flexible bracket being formed from a material having a first durometer hardness; and
  a cutting block positioned in the upper surface of the bracket, the cutting block comprising an interior surface and defining a slit, the slit configured to match a shape of a scalpel blade and to orient the scalpel blade in a plane that is transverse to a closest adjacent portion of a mounted annuloplasty ring, the interior surface being rigid and being formed of a material having a second durometer hardness higher than the first durometer hardness.

7. The tool of claim 6, the cutting block recessed into the upper surface of the bracket.

8. The tool of claim 7, the cutting block comprising an exterior surface, the exterior surface enveloped in the upper surface of the bracket, the interior surface defining the slit.

9. The tool of claim 8, the cutting block entirely made of the material having the second durometer hardness.

10. The tool of claim 6, the cutting block interior surface comprising a coating, the coating selected from the group consisting of cyanoacrylates, acrylics, urethanes, and epoxies.

11. The tool of claim 6, further comprising a rigid connector attached to the flexible bracket, the connector comprising an attachment site for attachment of a grasping device, the connector being formed of a material having a third durometer hardness higher than the first durometer hardness.

12. The tool of claim 6, the flexible bracket being made of a material selected from the group consisting of thermoplastic elastomers, polyesters, polyamide polyether block amides, polyurethanes, urethanes, polyethylenes, polybutylenes, silicon, rubber, polyimides, nylons, fluorinated hydrocarbon polymers, silicon polyurethane copolymers, and thermoplastic vulcanizates.

13. The tool of claim 6 wherein a portion of the cutting block protrudes above the upper surface of the bracket.

14. A tool for holding and supporting an annuloplasty ring comprising:

a flexible bracket having an upper surface, a central portion, and an outer bracket portion, a portion of the upper surface forming an upper flange, the outer bracket portion including a radially outwardly facing annular surface disposed below the upper flange and adapted to receive the annuloplasty ring thereabout, the annular surface having a height that extends from the upper flange to a lower-most point on the annular surface, the flexible bracket being formed from a material having a first durometer hardness;

a rigid connector attached to the flexible bracket, the connector comprising an attachment site for attachment of a grasping device, the connector being formed of a material having a second durometer hardness higher than the first durometer hardness; and a cutting block positioned in the upper surface of the bracket, the cutting block comprising an interior surface and defining a slit, the slit configured to match a shape of a scalpel blade and to orient the scalpel blade in a plane that is transverse to a closest adjacent portion of a mounted annuloplasty ring, the interior surface being rigid and being formed of a material having a third durometer hardness higher than the first durometer hardness.

15. The tool of claim 14, the interior surface comprising a coating.

16. The tool of claim 15, the coating being formed of the material having the third durometer hardness.

17. The tool of claim 1, the at cutting block being entirely made of the material having the third durometer hardness.

18. The tool of claim 17, the cutting block comprising an exterior surface, the exterior surface enveloped in the upper surface of the bracket, the interior surface defining the slit.

* * * * *